(12) United States Patent
Little et al.

(10) Patent No.: US 8,148,496 B2
(45) Date of Patent: *Apr. 3, 2012

(54) MULTIVALENT ANTIBODY CONSTRUCTS

(75) Inventors: Melvyn Little, Neckargemund (DE); Sergej Kipriyanov, Heidelberg (DE)

(73) Assignee: Deutsches Krebsforschungszentrum, Heidelberg (DE)

( * ) Notice: Subject to any disclaimer, the term of this patent is extended or adjusted under 35 U.S.C. 154(b) by 304 days.

This patent is subject to a terminal disclaimer.

(21) Appl. No.: 12/367,219

(22) Filed: Feb. 6, 2009

(65) Prior Publication Data
US 2010/0099853 A1 Apr. 22, 2010

Related U.S. Application Data

(60) Division of application No. 11/546,262, filed on Oct. 10, 2006, now Pat. No. 7,507,796, which is a continuation of application No. 09/674,794, filed as application No. PCT/DE99/01350 on May 5, 1999, now Pat. No. 7,129,330.

(30) Foreign Application Priority Data

May 5, 1998 (DE) .................................. 198 19 846

(51) Int. Cl.
*C12P 21/08* (2006.01)
*A61K 39/00* (2006.01)
*C12P 21/06* (2006.01)

(52) U.S. Cl. ........... 530/387.3; 530/388.22; 530/388.73; 530/388.75; 424/135.1; 435/69.1

(58) Field of Classification Search .......................... None
See application file for complete search history.

(56) References Cited

U.S. PATENT DOCUMENTS

| | | | |
|---|---|---|---|
| 5,534,254 A | | 7/1996 | Huston et al. |
| 5,635,599 A | | 6/1997 | Pastan et al. |
| 5,837,242 A | | 11/1998 | Holliger et al. |
| 5,856,456 A | | 1/1999 | Whitlow et al. |
| 5,892,020 A | | 4/1999 | Mezes et al. |
| 6,096,289 A | * | 8/2000 | Goldenberg ................ 424/1.49 |
| 6,759,518 B1 | | 7/2004 | Kontermann et al. |
| 7,129,330 B1 | | 10/2006 | Little et al. |
| 7,507,796 B2 | * | 3/2009 | Little et al. ................ 530/387.3 |
| 2005/0004352 A1 | | 1/2005 | Kontermann et al. |
| 2007/0031436 A1 | | 2/2007 | Little et al. |

FOREIGN PATENT DOCUMENTS

| | | | |
|---|---|---|---|
| EP | 0952218 A2 | | 10/1999 |
| WO | WO 97/01580 | * | 1/1997 |

OTHER PUBLICATIONS

Coloma, et al. Design and production of novel tetravel bispecific antibodies. NatureBiotechnology. 1997; 15:159-163.
Csoka, et al. Activation of T cell cytotoxicity against autologous common acute lymphoblastic leukemia (cALL) blasts by CD3xCD19 bispecific antibody. Leukemia.
De Jonge, et al. Production and characterizaton of bispecific single-chain antibody fragments. Molecular Immunology. 1995; 32:1405-1412.
Gruber, et al. Efficient tumor cell lysis mediated by a bispecific single chain antibody expressed in *Escherichia coli*. Journal of Immunology. 1994; 152:5368-5374.
Holliger et al. "Diabodies": small bivalent and bispecific antibody fragments. Proc. Natl. Acad. Sci. 1993; 90:6444-48.
Kipriyanov, et al. Bispecific tandem diabody for tumor therapy with improved antigen binding and pharmacokinetics. Journal of Molecular Biology. 1999; 293:41-56.
Kipriyanov, et al. Rapid detection of recombinant antibody fragments directed against cell-surface antigens by flow cytometry. J. Immunol. Meth. 1996; 196:51-62.
Kipriyanov, et al. Two amino acid mutations in an anti-human CD3 single chain Fv antibody fragment that affect the yield on bacterial secretion but not the affinity. Protein Eng. 1997; 10:445-453.
Kurucz, et al. Retargeting f CTL by an efficiently refolded bispecific single-chain Fv dimer produced in bacteria. Journal of Immunology. 1995; 154:4576-4582.
Li, et al. Single chain human interleukin 5 and its asymmetric mutagenesis for mapping receptor binding sites. The J. Biol. Chem. 1996; 26:1817-1820.
Mack, et al. A small bispecific antibody construct expressed as a functional single-chain molecule with tumor cell cytotoxicity. Proceedings of the National Academy of Science of the United States. 1995; 92:7021-7025.

* cited by examiner

*Primary Examiner* — Peter J Reddig
*Assistant Examiner* — Yan Xiao
(74) *Attorney, Agent, or Firm* — Perkins Coie LLP; Patrick D. Morris

(57) ABSTRACT

The present invention relates to a multivalent $F_v$ antibody construct having at least four variable domains which are linked with each over via the peptide linkers 1, 2 and 3. The invention also concerns expression plasmids which code for such an $F_v$ antibody construct and a method of producing the $F_v$ antibody constructs as well as their use.

6 Claims, 13 Drawing Sheets

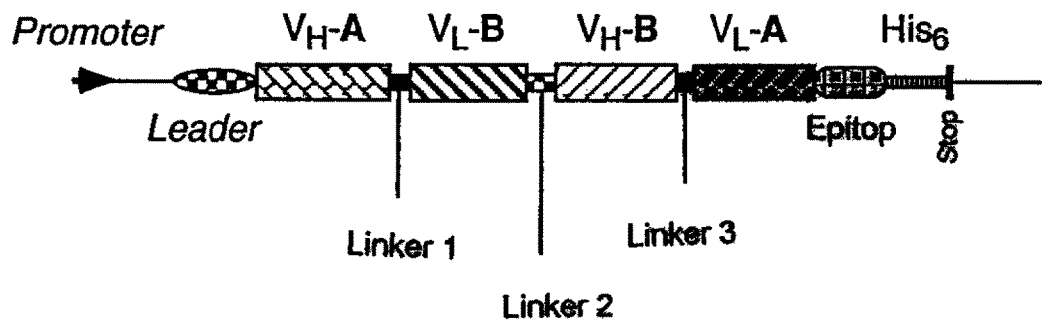
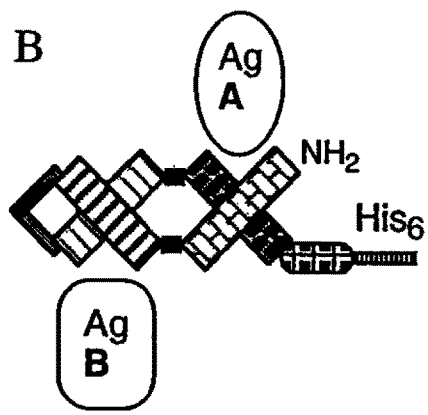
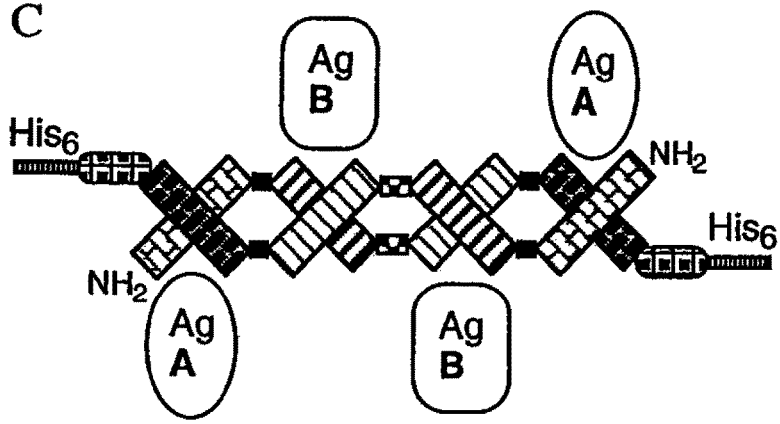
FIGURE 1

```
     EcoRI     RBS            PelB leader                                                                    NcoI
  1  GAATTCATTAAAGAGGAGAAATTAACCATGAAATACCTATTGCCTACGGCAGCCGCTGGATTGTTATTACTCGCTGCCCAACCAGCGATGGCCATGG
     1▸ M  K  Y  L  L  P  T  A  A  A  G  L  L  L  L  A  A  Q  P  A  M
                                        Frame-H1                                            VH anti-CD3
 92  CGCAGGTGCAACTGCAGCAGTCTGGGGCTGAACTGGCAAGACCTGGGGCCTCAGTGAAGATGTCCTGCAAGGCTTCTGGCTACACCTTTAC
 22▸ A  Q  V  Q  L  Q  Q  S  G  A  E  L  A  R  P  G  A  S  V  K  M  S  C  K  A  S  G  Y  T  F  T
         CDR-H1                              Frame-H2                                        CDR-H2
183  TAGGTTACACGGATGCACTGTGGGTAAAACAGAGGCCTGGACAGGGTCTTGAATGGATTGGATACATTAATCCTAGCCGTGGTTATAC
 52▸ R  Y  T  M  H  W  V  K  Q  R  P  G  Q  G  L  E  W  I  G  Y  I  N  P  S  R  G  Y  T
                                           Frame-H3
267  TAATTACAATCAGAAGTTCAAGGACAAGGCCACATTGACTACAGACAAATCCTCCAGCACAGCTTACATGCAACTGAGCAGCCTGAC
 80▸ N  Y  N  Q  K  F  K  D  K  A  T  L  T  T  D  K  S  S  S  T  A  Y  M  Q  L  S  S  L  T
                                              CDR-H3                                         Frame-H4
354  ATCTGAGGACTCTGCAGTCTATTACTGTGCAAGATATTATGATGATCATTACAGCCTTGACTACTGGGGCCAAGGCACCACTCTCA
109▸ S  E  D  S  A  V  Y  Y  C  A  R  Y  Y  D  D  H  Y  S  L  D  Y  W  G  Q  G  T  T  L
                                                       Linker 1                                          VL anti-CD19
440  CAGTCTCCTCAGCAAAACAACCAAGCTTGCTCACCCAAACTCCAGCTTCTTTGTCTGTGTCTCTAGGGCAG
138▸ T  V  S  S  A  K  T  T  P  K  L  G  G  D  I  L  L  T  Q  T  P  A  S  L  A  V  S  L  G  Q
             CH1                                 CDR-L1                                    Frame-L1
530  GGGCCACCATCTCCTGCAAGGCCAGCCAGTCTGTTGATTATGATGGTGATAGTTATTTGAACTGGTACCAACAGATTCCAGGAC
168▸ R  A  T  I  S  C  K  A  S  Q  S  V  D  Y  D  G  D  S  Y  L  N  W  Y  Q  Q  I  P  G
                                                     CDR-L2                                    Frame-L3
614  AGCCTCCAAAACTCCTCATCTATGATGCATCCAATCTAGTTTCTGGGATCCCCAGTTTAGTGGCAGTGGGTCTGGGACAGACTTT
196▸ Q  P  P  K  L  L  I  Y  D  A  S  N  L  V  S  G  I  P  F  S  G  S  G  S  G  T  D  F
                                                              CDR-L3                                           Frame-L4
702  CACCCTCAACATCATCCCTGAGAAGGTGGATGCTGCAACCTATCACTGTCAGCAAAGTACTGAGGATCCGTGGACGTTCGGTGGA
225▸ T  L  N  I  H  P  V  E  K  V  D  A  A  T  Y  H  C  Q  Q  S  T  E  D  P  W  T  F  G  G
                             C kappa                     NotI                                  Linker 2
790  GGCACCAAGCTGGAAATCAAACGGGCTGATGCCGCCGCTAAAGCGGCGGCTGGTGGTAGCGGTGGTGGCGGC
255▸ G  T  K  L  E  I  K  R  A  D  A  A  A  K  G  G  G  S  G  G  G  G  G
                                                      PvuII          Frame-H1                      VH anti-CD19
874  TCCGGTGGTGGTGGTAGCCAGGTGCAGCTGCAGCAGTCTGGGGCAGAGCTTGTGAGGCCAGGGGCCTCAGTCAAGATTTCCTGCAAGG
283▸ S  G  G  G  G  S  Q  V  Q  L  Q  Q  S  G  A  E  L  V  R  P  G  S  S  V  K  I  S  C  K
```

FIGURE 5A

```
                                                                                    CDR-H1                                Frame-H2                                                   CDR-H2
 962  CTTCTGGCTATGCATTCAGTAGCTACTGGATGAACTGGGTGAAGCAGAGGCCTGGACAGGGTCTTGAGTGGATTGGACAGATTTGGC
 312▸  A  S  G  Y  A  F  S  S  Y  W  M  N  W  V  K  Q  R  P  G  Q  G  L  E  W  I  G  Q  I  W PstI                Frame-H3
1049  CTGGAGATGGTGATACTAACTACTACAATGGAAAGTTCAAGGGTAAGGCCACTCTGACTGCAGACGAATCCTCCAGCACAGCCTACA
 341▸  P  G  D  G  D  T  N  Y  Y  N  G  K  F  K  G  K  A  T  L  T  A  D  E  S  S  S  T  A  Y
                                                                            CDR-H3
1133  TGCAACTCAGCAGCCTAGCATCTGAGGACTCTGCGGTCTATTTCTGTGCAAGACGGAGAACTACGAAGTTAGGCCGTTATTACTAT
 369▸  M  Q  L  S  S  L  A  S  E  D  S  A  V  Y  F  C  A  R  R  E  T  T  V  G  R  Y  Y  Y Frame-H4                                                         Linker 1                              Frame-L1
1219  GCTATGGACTACTGGGGTCAAGGGACCTCAGTCACCGTCTCCTCAGGTGGCGGTGGCAAGCTTGGTGGAGGCGGTTCAGGCGGAGGTGGCTCTGGCGGTGGCGGATATCGTCGTCACTC
 398▸  A  M  D  Y  W  G  Q  G  T  S  V  T  V  S  S  A  K  T  T  P  K  L  G  G  D  I  V  L  T
     VL anti-CD3                                                                                           CDR-L1
1307  AGTCCAGCAGAATCATGTCTGCATCTCCAGGGGAGAAGGTCACCATGACCTGCAGTGCCAGCTCAAGTGTAAGTTACATGAACTGG
 427▸  Q  S  P  A  I  M  S  A  S  P  G  E  K  V  T  M  T  C  S  A  S  S  S  V  S  Y  M  N  W CDR-L2                                  Frame-L3
1393  TACCAGCAGAAGTCAGGCACCTCCCCCAAAAGATGGATTTATGACACATCCAAACTGGCTTCTGGAGTCCCTGCTCACTTCAGGGGCA
 456▸  Y  Q  Q  K  S  G  T  S  P  K  R  W  I  Y  D  T  S  K  L  A  S  G  V  P  A  H  F  R  G
                                                                                                   CDR-L3
1481  GTGGGTCTGGGACCTCTTACTCTCTCACAATCAGCAGCATGGAGGCTGAAGATGCTGCCACTTATTACTGCCAGCAGTGGAGTAGTAA
 485▸  S  G  S  G  T  S  Y  S  L  T  I  S  S  M  E  A  E  D  A  A  T  Y  Y  C  Q  Q  W  S  S  N
                     Frame-L4                                          C kappa                                   c-myc epitope
1569  CCCCATTCACGTTCGGCTCGGGGACAAAGTTGGAAATAAAACCGGGCTGATCCGATCGAACAAAAGCTGAACATGAATCCGATCTTCAG
 514▸  P  F  T  F  G  S  G  T  K  L  E  I  N  R  A  D  T  A  P  T  G  S  E  Q  K  L  I  S
                                His6 tail           XbaI
1655  AAGAAGACCTAAACTCACCATCACCATCACCATCACTAATCTAGA
 543▸  E  E  D  L  N  S  H  H  H  H  H  H  .

```
941  ATGAGATTTCCTTCAATTTTTACTGCTGTTTTATTCGCAGCATCCTCCGCATTAGCTGCTCCAGTCAACACTAC
  1▶ M   R   F   P   S   I   F   T   A   V   L   F   A   A   S   S   A   L   A   A   P   V   N   T   T
                                        alpha-factor signal
1015 AACAGAAGATGAAACGGCACAAATTCCGGCTGAAGCTGTCATCGGTTACTCAGATTTAGAAGGGGATTTCGATG
 25▶ T   E   D   E   T   A   Q   I   P   A   E   A   V   I   G   Y   S   D   L   E   G   D   F   D 1089 TTGCTGTTTTGCCATTTTCCAACAGCACAAATAACGGGTTATTGTTTATAAATACTACTATTGCCAGCATTGCT
 50▶ V   A   V   L   P   F   S   N   S   T   N   N   G   L   L   F   I   N   T   T   I   A   S   I   A EcoRI
                         Xhol                              ◆     ◆
1163 GCTAAAGAAGAAGGGGTATCTCTCGAGAAAAGAGAGGCTGAAGCTGAATTCCAGGTGCAACTGCAGCAGTC
 75▶ A   K   E   E   G   V   S   L   E   K   R   E   A   E   A   E   F   Q   V   Q   L   Q   Q   S
     VH anti-CD3
1234 TGGGGCTGAACTGGCAAGACCTGGGGCCTCAGTGAAGATGTCCTGCAAGGCTTCT
 98▶ G   A   E   L   A   R   P   G   A   S   V   K   M   S   C   K   A   S
```

FIGURE 7

```
941  ATGAGATTTCCTTCAATTTTTACTGCTGTTTTATTCGCAGCATCCTCCGCATTAGCTGCTCCAGTCAACACTAC
  1▶  M   R   F   P   S   I   F   T   A   V   L   F   A   A   S   S   A   L   A   A   P   V   N   T   T
                                           alpha-factor signal
1015 AACAGAAGATGAAACGGCACAAATTCCGGCTGAAGCTGTCATCGGTTACTCAGATTTAGAAGGGGATTTCGATG
 25▶  T   E   D   E   T   A   Q   I   P   A   E   A   V   I   G   Y   S   D   L   E   G   D   F   D
                                                                                               BsrDI
1089 TTGCTGTTTTGCCATTTTCCAACAGCACAAATAACGGGTTATTGTTTATAAATACTACTATTGCCAGCATTGCT
 50▶  V   A   V   L   P   F   S   N   S   T   N   N   G   L   L   F   I   N   T   T   I   A   S   I   A
                                                              EcoRI
                              XhoI              ♦      ♦
1163 GCTAAAGAAGAAGGGGTATCTCTCGAGAAAAGAGAGGCTGAAGCTGAATTCATGGCGCAGGTGCAACTGCAG
 75▶  A   K   E   E   G   V   S   L   E   K   R   E   A   E   A   E   F   M   A   Q   V   Q   L   Q
             VH anti-CD3
1235 CAGTCTGGGGCTGAACTGGCAAGACCTGGGGCCTCAGTGAAGATGTCCTGCAAGGCTTCT
 99▶  Q   S   G   A   E   L   A   R   P   G   A   S   V   K   M   S   C   K   A   S

                        SEQUENCE LISTING

<160> NUMBER OF SEQ ID NOS: 23

<210> SEQ ID NO 1
<211> LENGTH: 1698
<212> TYPE: DNA
<213> ORGANISM: Artificial Sequence
<220> FEATURE:
<223> OTHER INFORMATION: Plasmid pDISC3x19-LL
<220> FEATURE:
<221> NAME/KEY: CDS
<222> LOCATION: (28)..(1689)

<400> SEQUENCE: 1
gaattcatta aagaggagaa attaacc atg aaa tac cta ttg cct acg gca gcc        54
                        Met Lys Tyr Leu Leu Pro Thr Ala Ala
                          1               5 gct ggc ttg ctg ctg ctg gca gct cag ccg gcc atg gcg cag gtg caa         102
Ala Gly Leu Leu Leu Leu Ala Ala Gln Pro Ala Met Ala Gln Val Gln
 10                  15                  20                  25 ctg cag cag tct ggg gct gaa ctg gca aga cct ggg gcc tca gtg aag         150
Leu Gln Gln Ser Gly Ala Glu Leu Ala Arg Pro Gly Ala Ser Val Lys
                 30                  35                  40 atg tcc tgc aag gct tct ggc tac acc ttt act agg tac acg atg cac         198
Met Ser Cys Lys Ala Ser Gly Tyr Thr Phe Thr Arg Tyr Thr Met His
             45                  50                  55 tgg gta aaa cag agg cct gga cag ggt ctg gaa tgg att gga tac att         246
Trp Val Lys Gln Arg Pro Gly Gln Gly Leu Glu Trp Ile Gly Tyr Ile
         60                  65                  70 aat cct agc cgt ggt tat act aat tac aat cag aag ttc aag gac aag         294
Asn Pro Ser Arg Gly Tyr Thr Asn Tyr Asn Gln Lys Phe Lys Asp Lys
     75                  80                  85 gcc aca ttg act aca gac aaa tcc tcc agc aca gcc tac atg caa ctg         342
Ala Thr Leu Thr Thr Asp Lys Ser Ser Ser Thr Ala Tyr Met Gln Leu
 90                  95                 100                 105 agc agc ctg aca tct gag gac tct gca gtc tat tac tgt gca aga tat         390
Ser Ser Leu Thr Ser Glu Asp Ser Ala Val Tyr Tyr Cys Ala Arg Tyr
                110                 115                 120 tat gat gat cat tac agc ctt gac tac tgg ggc caa ggc acc act ctc         438
Tyr Asp Asp His Tyr Ser Leu Asp Tyr Trp Gly Gln Gly Thr Thr Leu
            125                 130                 135
```

```
aca gtc tcc tca gcc aaa aca aca ccc aag ctt ggc ggt gat atc ttg      486
Thr Val Ser Ser Ala Lys Thr Thr Pro Lys Leu Gly Gly Asp Ile Leu
        140                 145                 150 ctc acc caa act cca gct tct ttg gct gtg tct cta ggg cag agg gcc      534
Leu Thr Gln Thr Pro Ala Ser Leu Ala Val Ser Leu Gly Gln Arg Ala
        155                 160                 165 acc atc tcc tgc aag gcc agc caa agt gtt gat tat gat ggt gat agt      582
Thr Ile Ser Cys Lys Ala Ser Gln Ser Val Asp Tyr Asp Gly Asp Ser
170                 175                 180                 185 tat ttg aac tgg tac caa cag att cca gga cag cca ccc aaa ctc ctc      630
Tyr Leu Asn Trp Tyr Gln Gln Ile Pro Gly Gln Pro Pro Lys Leu Leu
                190                 195                 200 atc tat gat gca tcc aat cta gtt tct ggg atc cca ccc agg ttt agt      678
Ile Tyr Asp Ala Ser Asn Leu Val Ser Gly Ile Pro Pro Arg Phe Ser
            205                 210                 215 ggc agt ggg tct ggg aca gac ttc acc ctc aac atc cat cct gtg gag      726
Gly Ser Gly Ser Gly Thr Asp Phe Thr Leu Asn Ile His Pro Val Glu
                220                 225                 230 aag gtg gat gct gca acc tat cac tgt cag caa agt act gag gat ccg      774
Lys Val Asp Ala Ala Thr Tyr His Cys Gln Gln Ser Thr Glu Asp Pro
            235                 240                 245 tgg acg ttc ggt gga ggc acc aag ctg gaa atc aaa cgg gct gat gct      822
Trp Thr Phe Gly Gly Gly Thr Lys Leu Glu Ile Lys Arg Ala Asp Ala
250                 255                 260                 265 gcg gcc gct ggt ggt ggt tct ggc ggt ggt agc ggt ggt ggc              870
Ala Ala Ala Gly Gly Gly Ser Gly Gly Gly Ser Gly Gly Gly
                270                 275                 280 ggc tcc ggt ggt ggt ggt agc cag gtg cag ctg cag cag tct ggg gct      918
Gly Ser Gly Gly Gly Gly Ser Gln Val Gln Leu Gln Gln Ser Gly Ala
            285                 290                 295 gag ctg gtg agg cct ggg tcc tca gtg aag att tcc tgc aag gct tct      966
Glu Leu Val Arg Pro Gly Ser Ser Val Lys Ile Ser Cys Lys Ala Ser
                300                 305                 310 ggc tat gca ttc agt agc tac tgg atg aac tgg gtg aag cag agg cct     1014
Gly Tyr Ala Phe Ser Ser Tyr Trp Met Asn Trp Val Lys Gln Arg Pro
            315                 320                 325 gga cag ggt ctt gag tgg att gga cag att tgg cct gga gat ggt gat     1062
Gly Gln Gly Leu Glu Trp Ile Gly Gln Ile Trp Pro Gly Asp Gly Asp
330                 335                 340                 345 act aac tac aat gga aag ttc aag ggt aaa gcc act ctg act gca gac     1110
Thr Asn Tyr Asn Gly Lys Phe Lys Gly Lys Ala Thr Leu Thr Ala Asp
                350                 355                 360 gaa tcc tcc agc aca gcc tac atg caa ctc agc agc cta gca tct gag     1158
Glu Ser Ser Ser Thr Ala Tyr Met Gln Leu Ser Ser Leu Ala Ser Glu
            365                 370                 375 gac tct gcg gtc tat ttc tgt gca aga cgg gag act acg acg gta ggc     1206
Asp Ser Ala Val Tyr Phe Cys Ala Arg Arg Glu Thr Thr Thr Val Gly
                380                 385                 390 cgt tat tac tat gct atg gac tac tgg ggt caa gga acc tca gtc acc     1254
Arg Tyr Tyr Tyr Ala Met Asp Tyr Trp Gly Gln Gly Thr Ser Val Thr
            395                 400                 405 gtc tcc tca gcc aaa aca aca ccc aag ctt ggc ggt gat atc gtg ctc     1302
Val Ser Ser Ala Lys Thr Thr Pro Lys Leu Gly Gly Asp Ile Val Leu
410                 415                 420                 425 act cag tct cca gca atc atg tct gca tct cca ggg gag aag gtc acc     1350
Thr Gln Ser Pro Ala Ile Met Ser Ala Ser Pro Gly Glu Lys Val Thr
                430                 435                 440 atg acc tgc agt gcc agc tca agt gta agt tac atg aac tgg tac cag     1398
Met Thr Cys Ser Ala Ser Ser Val Ser Tyr Met Asn Trp Tyr Gln
            445                 450                 455
```

-continued

| | | | | | | | | | | | | | | |
|---|---|---|---|---|---|---|---|---|---|---|---|---|---|---|
| cag | aag | tca | ggc | acc | tcc | ccc | aaa | aga | tgg | att | tat | gac | aca | tcc | aaa | 1446 |
| Gln | Lys | Ser | Gly | Thr | Ser | Pro | Lys | Arg | Trp | Ile | Tyr | Asp | Thr | Ser | Lys |
| | 460 | | | | | 465 | | | | | 470 | | | | |
| ctg | gct | tct | gga | gtc | cct | gct | cac | ttc | agg | ggc | agt | ggg | tct | ggg | acc | 1494 |
| Leu | Ala | Ser | Gly | Val | Pro | Ala | His | Phe | Arg | Gly | Ser | Gly | Ser | Gly | Thr |
| 475 | | | | | 480 | | | | | 485 | | | | | |
| tct | tac | tct | ctc | aca | atc | agc | ggc | atg | gag | gct | gaa | gat | gct | gcc | act | 1542 |
| Ser | Tyr | Ser | Leu | Thr | Ile | Ser | Gly | Met | Glu | Ala | Glu | Asp | Ala | Ala | Thr |
| 490 | | | | | 495 | | | | | 500 | | | | | 505 |
| tat | tac | tgc | cag | cag | tgg | agt | agt | aac | cca | ttc | acg | ttc | ggc | tcg | ggg | 1590 |
| Tyr | Tyr | Cys | Gln | Gln | Trp | Ser | Ser | Asn | Pro | Phe | Thr | Phe | Gly | Ser | Gly |
| | | | 510 | | | | | 515 | | | | | 520 | | |
| aca | aag | ttg | gaa | ata | aac | cgg | gct | gat | act | gca | cca | act | gga | tcc | gaa | 1638 |
| Thr | Lys | Leu | Glu | Ile | Asn | Arg | Ala | Asp | Thr | Ala | Pro | Thr | Gly | Ser | Glu |
| | | | 525 | | | | | 530 | | | | | 535 | | |
| caa | aag | ctg | atc | tca | gaa | gaa | gac | cta | aac | tca | cat | cac | cat | cac | cat | 1686 |
| Gln | Lys | Leu | Ile | Ser | Glu | Glu | Asp | Leu | Asn | Ser | His | His | His | His | His |
| | | | 540 | | | | | 545 | | | | | 550 | | |
| cac | taatctaga | | | | | | | | | | | | | | | 1698 |
| His | | | | | | | | | | | | | | | |

<210> SEQ ID NO 2
<211> LENGTH: 554
<212> TYPE: PRT
<213> ORGANISM: Artificial Sequence
<220> FEATURE:
<223> OTHER INFORMATION: Synthetic Construct

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
            20                  25                  30

Leu Ala Arg Pro Gly Ala Ser Val Lys Met Ser Cys Lys Ala Ser Gly
        35                  40                  45

Tyr Thr Phe Thr Arg Tyr Thr Met His Trp Val Lys Gln Arg Pro Gly
    50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
                85                  90                  95

Ser Ser Ser Thr Ala Tyr Met Gln Leu Ser Ser Leu Thr Ser Glu Asp
            100                 105                 110

Ser Ala Val Tyr Tyr Cys Ala Arg Tyr Tyr Asp Asp His Tyr Ser Leu
        115                 120                 125

Asp Tyr Trp Gly Gln Gly Thr Thr Leu Thr Val Ser Ser Ala Lys Thr
    130                 135                 140

Thr Pro Lys Leu Gly Gly Asp Ile Leu Leu Thr Gln Thr Pro Ala Ser
145                 150                 155                 160

Leu Ala Val Ser Leu Gly Gln Arg Ala Thr Ile Ser Cys Lys Ala Ser
                165                 170                 175

Gln Ser Val Asp Tyr Asp Gly Asp Ser Tyr Leu Asn Trp Tyr Gln Gln
            180                 185                 190

Ile Pro Gly Gln Pro Pro Lys Leu Leu Ile Tyr Asp Ala Ser Asn Leu
        195                 200                 205

Val Ser Gly Ile Pro Pro Arg Phe Ser Gly Ser Gly Ser Gly Thr Asp
    210                 215                 220

Phe Thr Leu Asn Ile His Pro Val Glu Lys Val Asp Ala Ala Thr Tyr

```
                    225                 230                 235                 240

His Cys Gln Gln Ser Thr Glu Asp Pro Trp Thr Phe Gly Gly Gly Thr
                245                 250                 255

Lys Leu Glu Ile Lys Arg Ala Asp Ala Ala Ala Gly Gly Gly Gly
            260                 265                 270

Ser Gly Gly Gly Gly Ser Gly Gly Gly Gly Ser Gly Gly Gly Gly Ser
        275                 280                 285

Gln Val Gln Leu Gln Gln Ser Gly Ala Glu Leu Val Arg Pro Gly Ser
    290                 295                 300

Ser Val Lys Ile Ser Cys Lys Ala Ser Gly Tyr Ala Phe Ser Ser Tyr
305                 310                 315                 320

Trp Met Asn Trp Val Lys Gln Arg Pro Gly Gln Gly Leu Glu Trp Ile
                325                 330                 335

Gly Gln Ile Trp Pro Gly Asp Gly Asp Thr Asn Tyr Asn Gly Lys Phe
            340                 345                 350

Lys Gly Lys Ala Thr Leu Thr Ala Asp Glu Ser Ser Ser Thr Ala Tyr
        355                 360                 365

Met Gln Leu Ser Ser Leu Ala Ser Glu Asp Ser Ala Val Tyr Phe Cys
    370                 375                 380

Ala Arg Arg Glu Thr Thr Thr Val Gly Arg Tyr Tyr Tyr Ala Met Asp
385                 390                 395                 400

Tyr Trp Gly Gln Gly Thr Ser Val Thr Val Ser Ser Ala Lys Thr Thr
                405                 410                 415

Pro Lys Leu Gly Gly Asp Ile Val Leu Thr Gln Ser Pro Ala Ile Met
            420                 425                 430

Ser Ala Ser Pro Gly Glu Lys Val Thr Met Thr Cys Ser Ala Ser Ser
        435                 440                 445

Ser Val Ser Tyr Met Asn Trp Tyr Gln Gln Lys Ser Gly Thr Ser Pro
    450                 455                 460

Lys Arg Trp Ile Tyr Asp Thr Ser Lys Leu Ala Ser Gly Val Pro Ala
465                 470                 475                 480

His Phe Arg Gly Ser Gly Ser Gly Thr Ser Tyr Ser Leu Thr Ile Ser
                485                 490                 495

Gly Met Glu Ala Glu Asp Ala Ala Thr Tyr Tyr Cys Gln Gln Trp Ser
            500                 505                 510

Ser Asn Pro Phe Thr Phe Gly Ser Gly Thr Lys Leu Glu Ile Asn Arg
        515                 520                 525

Ala Asp Thr Ala Pro Thr Gly Ser Glu Gln Lys Leu Ile Ser Glu Glu
    530                 535                 540

Asp Leu Asn Ser His His His His His His
545                 550

<210> SEQ ID NO 3
<211> LENGTH: 1653
<212> TYPE: DNA
<213> ORGANISM: Artificial Sequence
<220> FEATURE:
<223> OTHER INFORMATION: Plasmid pDISC3x19-SL
<220> FEATURE:
<221> NAME/KEY: CDS
<222> LOCATION: (28)..(1644)

<400> SEQUENCE: 3
gaattcatta aagaggagaa attaacc atg aaa tac cta ttg cct acg gca gcc      54
                            Met Lys Tyr Leu Leu Pro Thr Ala Ala
                              1               5 gct ggc ttg ctg ctg ctg gca gct cag ccg gcc atg gcg cag gtg caa     102
```

```
            Ala Gly Leu Leu Leu Leu Ala Ala Gln Pro Ala Met Ala Gln Val Gln
            10              15                  20                  25 ctg cag cag tct ggg gct gaa ctg gca aga cct ggg gcc tca gtg aag         150
Leu Gln Gln Ser Gly Ala Glu Leu Ala Arg Pro Gly Ala Ser Val Lys
                30                  35                  40 atg tcc tgc aag gct tct ggc tac acc ttt act agg tac acg atg cac         198
Met Ser Cys Lys Ala Ser Gly Tyr Thr Phe Thr Arg Tyr Thr Met His
            45                  50                  55 tgg gta aaa cag agg cct gga cag ggt ctg gaa tgg att gga tac att         246
Trp Val Lys Gln Arg Pro Gly Gln Gly Leu Glu Trp Ile Gly Tyr Ile
        60                  65                  70 aat cct agc cgt ggt tat act aat tac aat cag aag ttc aag gac aag         294
Asn Pro Ser Arg Gly Tyr Thr Asn Tyr Asn Gln Lys Phe Lys Asp Lys
    75                  80                  85 gcc aca ttg act aca gac aaa tcc tcc agc aca gcc tac atg caa ctg         342
Ala Thr Leu Thr Thr Asp Lys Ser Ser Ser Thr Ala Tyr Met Gln Leu
90                  95                  100                 105 agc agc ctg aca tct gag gac tct gca gtc tat tac tgt gca aga tat         390
Ser Ser Leu Thr Ser Glu Asp Ser Ala Val Tyr Tyr Cys Ala Arg Tyr
                110                 115                 120 tat gat gat cat tac agc ctt gac tac tgg ggc caa ggc acc act ctc         438
Tyr Asp Asp His Tyr Ser Leu Asp Tyr Trp Gly Gln Gly Thr Thr Leu
            125                 130                 135 aca gtc tcc tca gcc aaa aca aca ccc aag ctt ggc ggt gat atc ttg         486
Thr Val Ser Ser Ala Lys Thr Thr Pro Lys Leu Gly Gly Asp Ile Leu
        140                 145                 150 ctc acc caa act cca gct tct ttg gct gtg tct cta ggg cag agg gcc         534
Leu Thr Gln Thr Pro Ala Ser Leu Ala Val Ser Leu Gly Gln Arg Ala
    155                 160                 165 acc atc tcc tgc aag gcc agc caa agt gtt gat tat gat ggt gat agt         582
Thr Ile Ser Cys Lys Ala Ser Gln Ser Val Asp Tyr Asp Gly Asp Ser
170                 175                 180                 185 tat ttg aac tgg tac caa cag att cca gga cag cca ccc aaa ctc ctc         630
Tyr Leu Asn Trp Tyr Gln Gln Ile Pro Gly Gln Pro Pro Lys Leu Leu
                190                 195                 200 atc tat gat gca tcc aat cta gtt tct ggg atc cca ccc agg ttt agt         678
Ile Tyr Asp Ala Ser Asn Leu Val Ser Gly Ile Pro Pro Arg Phe Ser
            205                 210                 215 ggc agt ggg tct ggg aca gac ttc acc ctc aac atc cat cct gtg gag         726
Gly Ser Gly Ser Gly Thr Asp Phe Thr Leu Asn Ile His Pro Val Glu
        220                 225                 230 aag gtg gat gct gca acc tat cac tgt cag caa agt act gag gat ccg         774
Lys Val Asp Ala Ala Thr Tyr His Cys Gln Gln Ser Thr Glu Asp Pro
    235                 240                 245 tgg acg ttc ggt gga ggc acc aag ctg gaa atc aaa cgg gct gat gct         822
Trp Thr Phe Gly Gly Gly Thr Lys Leu Glu Ile Lys Arg Ala Asp Ala
250                 255                 260                 265 gcg gcc gct ggt ggc cca ggg tcg cag gtg cag ctg cag cag tct ggg         870
Ala Ala Ala Gly Gly Pro Gly Ser Gln Val Gln Leu Gln Gln Ser Gly
                270                 275                 280 gct gag ctg gtg agg cct ggg tcc tca gtg aag att tcc tgc aag gct         918
Ala Glu Leu Val Arg Pro Gly Ser Ser Val Lys Ile Ser Cys Lys Ala
            285                 290                 295 tct ggc tat gca ttc agt agc tac tgg atg aac tgg gtg aag cag agg         966
Ser Gly Tyr Ala Phe Ser Ser Tyr Trp Met Asn Trp Val Lys Gln Arg
        300                 305                 310 cct gga cag ggt ctt gag tgg att gga cag att tgg cct gga gat ggt        1014
Pro Gly Gln Gly Leu Glu Trp Ile Gly Gln Ile Trp Pro Gly Asp Gly
    315                 320                 325 gat act aac tac aat gga aag ttc aag ggt aaa gcc act ctg act gca        1062
```

```
Asp Thr Asn Tyr Asn Gly Lys Phe Lys Gly Lys Ala Thr Leu Thr Ala
330                 335                 340                 345 gac gaa tcc tcc agc aca gcc tac atg caa ctc agc agc cta gca tct    1110
Asp Glu Ser Ser Ser Thr Ala Tyr Met Gln Leu Ser Ser Leu Ala Ser
                350                 355                 360 gag gac tct gcg gtc tat ttc tgt gca aga cgg gag act acg acg gta    1158
Glu Asp Ser Ala Val Tyr Phe Cys Ala Arg Arg Glu Thr Thr Thr Val
                365                 370                 375 ggc cgt tat tac tat gct atg gac tac tgg ggt caa gga acc tca gtc    1206
Gly Arg Tyr Tyr Tyr Ala Met Asp Tyr Trp Gly Gln Gly Thr Ser Val
                380                 385                 390 acc gtc tcc tca gcc aaa aca aca ccc aag ctt ggc ggt gat atc gtg    1254
Thr Val Ser Ser Ala Lys Thr Thr Pro Lys Leu Gly Gly Asp Ile Val
        395                 400                 405 ctc act cag tct cca gca atc atg tct gca tct cca ggg gag aag gtc    1302
Leu Thr Gln Ser Pro Ala Ile Met Ser Ala Ser Pro Gly Glu Lys Val
410                 415                 420                 425 acc atg acc tgc agt gcc agc tca agt gta agt tac atg aac tgg tac    1350
Thr Met Thr Cys Ser Ala Ser Ser Val Ser Tyr Met Asn Trp Tyr
                430                 435                 440 cag cag aag tca ggc acc tcc ccc aaa aga tgg att tat gac aca tcc    1398
Gln Gln Lys Ser Gly Thr Ser Pro Lys Arg Trp Ile Tyr Asp Thr Ser
                445                 450                 455 aaa ctg gct tct gga gtc cct gct cac ttc agg ggc agt ggg tct ggg    1446
Lys Leu Ala Ser Gly Val Pro Ala His Phe Arg Gly Ser Gly Ser Gly
                460                 465                 470 acc tct tac tct ctc aca atc agc ggc atg gag gct gaa gat gct gcc    1494
Thr Ser Tyr Ser Leu Thr Ile Ser Gly Met Glu Ala Glu Asp Ala Ala
        475                 480                 485 act tat tac tgc cag cag tgg agt agt aac cca ttc acg ttc ggc tcg    1542
Thr Tyr Tyr Cys Gln Gln Trp Ser Ser Asn Pro Phe Thr Phe Gly Ser
490                 495                 500                 505 ggg aca aag ttg gaa ata aac cgg gct gat act gca cca act gga tcc    1590
Gly Thr Lys Leu Glu Ile Asn Arg Ala Asp Thr Ala Pro Thr Gly Ser
                510                 515                 520 gaa caa aag ctg atc tca gaa gaa gac cta aac tca cat cac cat cac    1638
Glu Gln Lys Leu Ile Ser Glu Glu Asp Leu Asn Ser His His His His
                525                 530                 535 cat cac taatctaga                                                   1653
His His <210> SEQ ID NO 4
<211> LENGTH: 539
<212> TYPE: PRT
<213> ORGANISM: Artificial Sequence
<220> FEATURE:
<223> OTHER INFORMATION: Synthetic Construct

<400> SEQUENCE: 4

Met Lys Tyr Leu Leu Pro Thr Ala Ala Ala Gly Leu Leu Leu Leu Ala
1               5                   10                  15

Ala Gln Pro Ala Met Ala Gln Val Gln Leu Gln Gln Ser Gly Ala Glu
                20                  25                  30

Leu Ala Arg Pro Gly Ala Ser Val Lys Met Ser Cys Lys Ala Ser Gly
            35                  40                  45

Tyr Thr Phe Thr Arg Tyr Thr Met His Trp Val Lys Gln Arg Pro Gly
        50                  55                  60

Gln Gly Leu Glu Trp Ile Gly Tyr Ile Asn Pro Ser Arg Gly Tyr Thr
65                  70                  75                  80

Asn Tyr Asn Gln Lys Phe Lys Asp Lys Ala Thr Leu Thr Thr Asp Lys
```

```
                    85                  90                  95
Ser Ser Ser Thr Ala Tyr Met Gln Leu Ser Ser Leu Thr Ser Glu Asp
                100                 105                 110

Ser Ala Val Tyr Tyr Cys Ala Arg Tyr Tyr Asp Asp His Tyr Ser Leu
                115                 120                 125

Asp Tyr Trp Gly Gln Gly Thr Thr Leu Thr Val Ser Ser Ala Lys Thr
                130                 135                 140

Thr Pro Lys Leu Gly Gly Asp Ile Leu Leu Thr Gln Thr Pro Ala Ser
145                 150                 155                 160

Leu Ala Val Ser Leu Gly Gln Arg Ala Thr Ile Ser Cys Lys Ala Ser
                165                 170                 175

Gln Ser Val Asp Tyr Asp Gly Asp Ser Tyr Leu Asn Trp Tyr Gln Gln
                180                 185                 190

Ile Pro Gly Gln Pro Pro Lys Leu Leu Ile Tyr Asp Ala Ser Asn Leu
                195                 200                 205

Val Ser Gly Ile Pro Pro Arg Phe Ser Gly Ser Gly Ser Gly Thr Asp
                210                 215                 220

Phe Thr Leu Asn Ile His Pro Val Glu Lys Val Asp Ala Ala Thr Tyr
225                 230                 235                 240

His Cys Gln Gln Ser Thr Glu Asp Pro Trp Thr Phe Gly Gly Gly Thr
                245                 250                 255

Lys Leu Glu Ile Lys Arg Ala Asp Ala Ala Ala Gly Gly Pro Gly Gly
                260                 265                 270

Ser Gln Val Gln Leu Gln Gln Ser Gly Ala Glu Leu Val Arg Pro Gly
                275                 280                 285

Ser Ser Val Lys Ile Ser Cys Lys Ala Ser Gly Tyr Ala Phe Ser Ser
                290                 295                 300

Tyr Trp Met Asn Trp Val Lys Gln Arg Pro Gly Gln Gly Leu Glu Trp
305                 310                 315                 320

Ile Gly Gln Ile Trp Pro Gly Asp Gly Asp Thr Asn Tyr Asn Gly Lys
                325                 330                 335

Phe Lys Gly Lys Ala Thr Leu Thr Ala Asp Glu Ser Ser Ser Thr Ala
                340                 345                 350

Tyr Met Gln Leu Ser Ser Leu Ala Ser Glu Asp Ser Ala Val Tyr Phe
                355                 360                 365

Cys Ala Arg Arg Glu Thr Thr Thr Val Gly Arg Tyr Tyr Tyr Ala Met
                370                 375                 380

Asp Tyr Trp Gly Gln Gly Thr Ser Val Thr Val Ser Ser Ala Lys Thr
385                 390                 395                 400

Thr Pro Lys Leu Gly Gly Asp Ile Val Leu Thr Gln Ser Pro Ala Ile
                405                 410                 415

Met Ser Ala Ser Pro Gly Glu Lys Val Thr Met Thr Cys Ser Ala Ser
                420                 425                 430

Ser Ser Val Ser Tyr Met Asn Trp Tyr Gln Gln Lys Ser Gly Thr Ser
                435                 440                 445

Pro Lys Arg Trp Ile Tyr Asp Thr Ser Lys Leu Ala Ser Gly Val Pro
450                 455                 460

Ala His Phe Arg Gly Ser Gly Ser Gly Thr Ser Tyr Ser Leu Thr Ile
465                 470                 475                 480

Ser Gly Met Glu Ala Glu Asp Ala Ala Thr Tyr Tyr Cys Gln Gln Trp
                485                 490                 495

Ser Ser Asn Pro Phe Thr Phe Gly Ser Gly Thr Lys Leu Glu Ile Asn
                500                 505                 510
```

```
Arg Ala Asp Thr Ala Pro Thr Gly Ser Glu Gln Lys Leu Ile Ser Glu
        515                 520                 525

Glu Asp Leu Asn Ser His His His His His
    530                 535
```

<210> SEQ ID NO 5
<211> LENGTH: 57
<212> TYPE: DNA
<213> ORGANISM: Artificial Sequence
<220> FEATURE:
<223> OTHER INFORMATION: Primer

<400> SEQUENCE: 5
tatatactgc agctgcacct gcgaccctgg gccaccagcg gccgcagcat cagcccg        57

<210> SEQ ID NO 6
<211> LENGTH: 45
<212> TYPE: DNA
<213> ORGANISM: Artificial Sequence
<220> FEATURE:
<223> OTHER INFORMATION: Primer

<400> SEQUENCE: 6
ccgtgaattc caggtgcaac tgcagcagtc tggggctgaa ctggc        45

<210> SEQ ID NO 7
<211> LENGTH: 34
<212> TYPE: DNA
<213> ORGANISM: Artificial Sequence
<220> FEATURE:
<223> OTHER INFORMATION: Primer

<400> SEQUENCE: 7
ggtcgacgtt aaccgacaaa caacagataa aacg        34

<210> SEQ ID NO 8
<211> LENGTH: 348
<212> TYPE: DNA
<213> ORGANISM: Artificial Sequence
<220> FEATURE:
<223> OTHER INFORMATION: Fragment of plasmid pPIC-DISC-SL
<220> FEATURE:
<221> NAME/KEY: CDS
<222> LOCATION: (1)..(348)

<400> SEQUENCE: 8

```
atg aga ttt cct tca att ttt act gct gtt tta ttc gca gca tcc tcc        48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa        96
Ala Leu Ala Ala Pro Val Asn Thr Thr Thr Glu Asp Glu Thr Ala Gln
            20                  25                  30 att ccg gct gaa gct gtc atc ggt tac tca gat tta gaa ggg gat ttc        144
Ile Pro Ala Glu Ala Val Ile Gly Tyr Ser Asp Leu Glu Gly Asp Phe
        35                  40                  45 gat gtt gct gtt ttg cca ttt tcc aac agc aca aat aac ggg tta ttg        192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta        240
Phe Ile Asn Thr Thr Ile Ala Ser Ile Ala Ala Lys Glu Glu Gly Val
65                  70                  75                  80 tct ctc gag aaa aga gag gct gaa gct gaa ttc cag gtg caa ctg cag        288
Ser Leu Glu Lys Arg Glu Ala Glu Ala Glu Phe Gln Val Gln Leu Gln
                85                  90                  95 cag tct ggg gct gaa ctg gca aga cct ggg gcc tca gtg aag atg tcc        336
Gln Ser Gly Ala Glu Leu Ala Arg Pro Gly Ala Ser Val Lys Met Ser
```

```
                            Gln Ser Gly Ala Glu Leu Ala Arg Pro Gly Ala Ser Val Lys Met Ser
                                    100                 105                 110 tgc aag gct tct                                                                              348
Cys Lys Ala Ser
        115

<210> SEQ ID NO 9
<211> LENGTH: 116
<212> TYPE: PRT
<213> ORGANISM: Artificial Sequence
<220> FEATURE:
<223> OTHER INFORMATION: Synthetic Construct

<400> SEQUENCE: 9

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
            35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Gln Val Gln Leu Gln
                85                  90                  95

Gln Ser Gly Ala Glu Leu Ala Arg Pro Gly Ala Ser Val Lys Met Ser
            100                 105                 110

Cys Lys Ala Ser
        115

<210> SEQ ID NO 10
<211> LENGTH: 354
<212> TYPE: DNA
<213> ORGANISM: Artificial Sequence
<220> FEATURE:
<223> OTHER INFORMATION: Fragment of plasmid pPIC-DISC-LL
<220> FEATURE:
<221> NAME/KEY: CDS
<222> LOCATION: (1)..(354)

<400> SEQUENCE: 10 atg aga ttt cct tca att ttt act gct gtt tta ttc gca gca tcc tcc         48
Met Arg Phe Pro Ser Ile Phe Thr Ala Val Leu Phe Ala Ala Ser Ser
1               5                   10                  15 gca tta gct gct cca gtc aac act aca aca gaa gat gaa acg gca caa         96
Ala Leu Ala Ala Pro Val Asn Thr Thr Thr Glu Asp Glu Thr Ala Gln
                20                  25                  30 att ccg gct gaa gct gtc atc ggt tac tca gat tta gaa ggg gat ttc        144
Ile Pro Ala Glu Ala Val Ile Gly Tyr Ser Asp Leu Glu Gly Asp Phe
            35                  40                  45 gat gtt gct gtt ttg cca ttt tcc aac agc aca aat aac ggg tta ttg        192
Asp Val Ala Val Leu Pro Phe Ser Asn Ser Thr Asn Asn Gly Leu Leu
    50                  55                  60 ttt ata aat act act att gcc agc att gct gct aaa gaa gaa ggg gta        240
Phe Ile Asn Thr Thr Ile Ala Ser Ile Ala Ala Lys Glu Glu Gly Val
65                  70                  75                  80 tct ctc gag aaa aga gag gct gaa gct gaa ttc atg gcg cag gtg caa        288
Ser Leu Glu Lys Arg Glu Ala Glu Ala Glu Phe Met Ala Gln Val Gln
                85                  90                  95 ctg cag cag tct ggg gct gaa ctg gca aga cct ggg gcc tca gtg aag        336
Leu Gln Gln Ser Gly Ala Glu Leu Ala Arg Pro Gly Ala Ser Val Lys
```

```
                        100                 105                 110
atg tcc tgc aag gct tct                                                    354
Met Ser Cys Lys Ala Ser
        115
```

<210> SEQ ID NO 11
<211> LENGTH: 118
<212> TYPE: PRT
<213> ORGANISM: Artificial Sequence
<220> FEATURE:
<223> OTHER INFORMATION: Synthetic Construct

<400> SEQUENCE: 11

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Glu Lys Arg Glu Ala Glu Ala Glu Phe Met Ala Gln Val Gln
                85                  90                  95

Leu Gln Gln Ser Gly Ala Glu Leu Ala Arg Pro Gly Ala Ser Val Lys
            100                 105                 110

Met Ser Cys Lys Ala Ser
        115

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12
tcacacagaa ttcttagatc tattaaagag gagaaattaa cc                              42

<210> SEQ ID NO 13
<211> LENGTH: 40
<212> TYPE: DNA
<213> ORGANISM: Artificial Sequence
<220> FEATURE:
<223> OTHER INFORMATION: Primer

<400> SEQUENCE: 13
agcacacgat atcaccgcca agcttgggtg ttgttttggc                                 40

<210> SEQ ID NO 14
<211> LENGTH: 43
<212> TYPE: DNA
<213> ORGANISM: Artificial Sequence
<220> FEATURE:
<223> OTHER INFORMATION: Primer

<400> SEQUENCE: 14
agcacacaag cttggcggtg atatcttgct cacccaaact cca                             43

<210> SEQ ID NO 15
<211> LENGTH: 57
<212> TYPE: DNA

```
<213> ORGANISM: Artificial Sequence
<220> FEATURE:
<223> OTHER INFORMATION: Primer

<400> SEQUENCE: 15
agcacactct agagacacac agatctttag tgatggtgat ggtgatgtga gtttagg        57

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
cagccggcca tggcgcaggt gcaactgcag cag                                   33

<210> SEQ ID NO 17
<211> LENGTH: 102
<212> TYPE: DNA
<213> ORGANISM: Artificial Sequence
<220> FEATURE:
<223> OTHER INFORMATION: Primer

<400> SEQUENCE: 17
tatatactgc agctgcacct ggctaccacc accaccggag ccgccaccac cgctaccacc      60
gccgccagaa ccaccaccac cagcggccgc agcatcagcc cg                        102

<210> SEQ ID NO 18
<211> LENGTH: 5
<212> TYPE: PRT
<213> ORGANISM: Artificial Sequence
<220> FEATURE:
<223> OTHER INFORMATION: Embodiment of peptide linker 2

<400> SEQUENCE: 18

Gly Gly Pro Gly Ser
1               5

<210> SEQ ID NO 19
<211> LENGTH: 55
<212> TYPE: DNA
<213> ORGANISM: Artificial Sequence
<220> FEATURE:
<223> OTHER INFORMATION: Primer

<400> SEQUENCE: 19
cgaattctta agataagaag gagtttattg tgaaaaagtg gttattagct gcagg           55

<210> SEQ ID NO 20
<211> LENGTH: 40
<212> TYPE: DNA
<213> ORGANISM: Artificial Sequence
<220> FEATURE:
<223> OTHER INFORMATION: Primer

<400> SEQUENCE: 20
cgaattaagc ttcattattt aacctgtttc agtacgtcgg                            40

<210> SEQ ID NO 21
<211> LENGTH: 41
<212> TYPE: DNA
<213> ORGANISM: Artificial Sequence
<220> FEATURE:
<223> OTHER INFORMATION: Primer

<400> SEQUENCE: 21
```

```
cgaatttcta gataagaagg agaaattaac catgaaatac c                    41
```

<210> SEQ ID NO 22
<211> LENGTH: 40
<212> TYPE: DNA
<213> ORGANISM: Artificial Sequence
<220> FEATURE:
<223> OTHER INFORMATION: Primer

<400> SEQUENCE: 22

```
cgaattctta agctattagt gatggtgatg gtgatgtgag                      40
```

<210> SEQ ID NO 23
<211> LENGTH: 20
<212> TYPE: PRT
<213> ORGANISM: Artificial Sequence
<220> FEATURE:
<223> OTHER INFORMATION: Embodiment of peptide linker 2

<400> SEQUENCE: 23

```
Gly Gly Gly Gly Ser Gly Gly Gly Gly Ser Gly Gly Gly Gly Ser Gly
1               5                   10                  15

Gly Gly Gly Ser
            20
```

```

MULTIVALENT ANTIBODY CONSTRUCTS

CROSS-REFERENCE

This application is a divisional application of Ser. No. 11/546,262, filed Oct. 10, 2006, issued as U.S. Pat. No. 7,507,796 which is a continuation application of Ser. No. 09/674,794, filed Aug. 21, 2001, now U.S. Pat. No. 7,129,330 issued on Oct. 21, 2006, which is a national phase filing of Application No. PCT/DE99/01350, which was filed with the Patent Cooperation Treaty on May 5, 1999, and is entitled to priority of the German Patent Application 198 19 846.9, filed May 5, 1998.

FIELD OF THE INVENTION

The present invention relates to multi-valent $F_v$ antibody constructs, expression plasmids which code for them, and a method for producing the $F_v$ antibody constructs as well as the use thereof.

BACKGROUND OF THE INVENTION

Natural antibodies are dimers and are therefore referred to as bivalent. They have four variable domains, namely two $V_H$ domains and two $V_L$ domains. The variable domains serve as binding sites for an antigen, a binding site being formed from a $V_H$ domain and a $V_L$ domain. Natural antibodies recognize one antigen each, so that they are also referred to as monospecific. Furthermore, they also have constant domains which add to the stability of the natural antibodies. On the other hand, they are also co-responsible for undesired immune responses which result when natural antibodies of various animal species are administered mutually.

In order to avoid such immune responses, antibodies are constructed which lack the constant domains. In particular, these are antibodies which only comprise the variable domains. Such antibodies are designated $F_v$ antibody constructs. They are often available in the form of single-chain monomers paired with one another.

However, it showed that $F_v$ antibody constructs only have little stability. Therefore, their usability for therapeutic purposes is strongly limited.

Thus, it is the object of the present invention to provide an antibody by means of which undesired immune responses can be avoided. Furthermore, it shall have a stability which makes it usable for therapeutic uses.

According to the invention this is achieved by the subject matters defined in the claims.

SUMMARY OF THE INVENTION

The present invention relates to a multivalent a multi-valent $F_v$ antibody construct having at least four variable domains which are linked with each other via the peptide linkers 1, 2 and 3. The invention also concerns expression plasmids which code for an $F_v$ antibody construct and a method of producing the $F_v$ antibody constructs as well as their use.

BRIEF DESCRIPTION OF THE DRAWINGS

FIG. 1 shows the genetic organization of an $F_v$ antibody construct (A) according to the invention and schemes for forming a bivalent (B) or tetravalent $F_v$ antibody construct (C) Ag: antigen; His$_6$: six C-terminal histidine residues; stop: stop codon (TAA); $V_H$ and $V_L$: variable region of the heavy and light chains.

FIG. 5 shows the nucleotide sequence (SEQ ID NO:1) and the amino acid sequence derived therefrom (SEQ ID NO:2) of the bivalent $F_v$ antibody construct encoded by the expression plasmid pDISC3×19-LL. c-myc epitope: sequence coding for an epitope which is recognized by the antibody 9E10; CDR: region determining the complementarity; framework: framework region; His6 tail: sequence which codes for six C-terminal histidine residues; Pe1B leader: signal peptide sequence of the bacterial pectate lyase; RBS: ribosome binding site; $V_H$ and $V_L$: variable region of the heavy and light chains.

FIG. 6 shows the nucleotide sequence (SEQ ID NO:3) and the derived amino acid sequence (SEQ ID NO:4) of the tetravalent $F_v$ antibody construct encoded by the expression plasmid pDISC3×19-SL. c-myc epitope: sequence coding for an epitope which is recognized by the 9E10 antibody; CDR: region determining complementarity; framework: framework region; His6 tail: sequence coding for the six C-terminal histidine residues; Pe1B leader: signal peptide sequence of the bacterial pectate lyase; RBS: ribosome binding site; $V_H$ and $V_L$: variable region of the heavy and light chains.

FIG. 7 shows the nucleotide sequence (SEQ ID NO:8) and the derived amino acid sequence (SEQ ID NO:9) of a connection between a gene which codes for an α-factor leader sequence and a gene coding for the tetravalent $F_v$ antibody construct in the *Pichia* expression plasmid pPIC-DISC-SL. Alpha-factor signal: leader peptide sequence of the *Saccha-* romyces cerevisiae-α factor secretion signal; $V_H$: variable region of the heavy chain. Rhombs indicate the signal cleaving sites.

FIG. 8 shows the nucleotide sequence (SEQ ID NO:10) and the derived amino acid sequence (SEQ ID NO:11) of a connection between a gene coding for an α-factor leader sequence and a gene which codes for the bivalent $F_v$ antibody construct in the *Pichia* expression plasmid pPIC-DISC-LL. Alpha-factor signal: leader peptide sequence of the *Saccharomyces cerevisiae*-α-factor secretion signal; $V_H$: variable region of the heavy chain.

Figure 9:
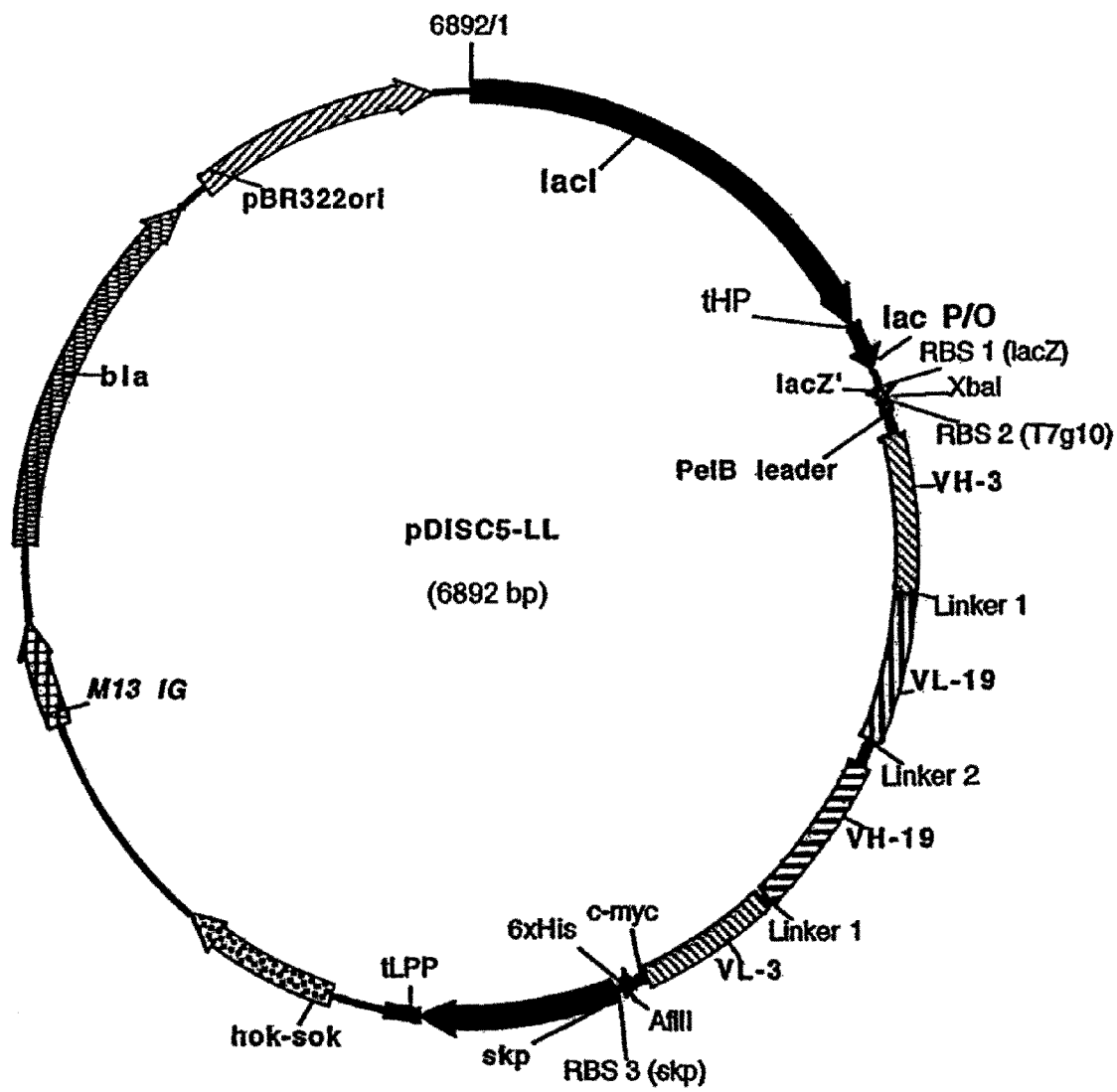

FIG. 9 shows a diagram of the expression plasmid pDISC5-LL. 6×His: sequence coding for six C-terminal histidine residues; bla: gene which codes for β-lactamase responsible for ampicillin resistance; bp: base pairs; c-myc: sequence coding for an epitope which is recognized by the 9E10 antibody; hok-sok: plasmid-stabilizing DNA locus; LacI: gene which codes for the Lac repressor; Lac P/O: wt lac-operon-promoter/operator, LacZ': gene which codes for the α-peptide of β-galactosidase, linker 1: sequence which codes for a GlyGly dipeptide connecting the $V_H$ and $V_L$ domains; linker 2: sequence which codes for a $(Gly_4Ser)_4$ polypeptide linking the hybrid scFv fragments; M13 IG: intergenic region of the M13 bacteriophage; pBR322ori: origin of DNA replication; Pe1-B leader: signal peptide sequence of the bacterial pectate lyase; rbs: ribosome binding site which originates from the *E. coli* lacZ gene (lacZ), from the bacteriophage T7 gene 10 (T7g10) or from the *E. coli* skp gene (skp), -skp: gene which codes for the bacterial periplasmic factor Skp/OmpH; tHP: strong transcription terminator; tIPP: transcription terminator; $V_H$ and $V_L$: variable region of the heavy and light chains.

Figure 10:
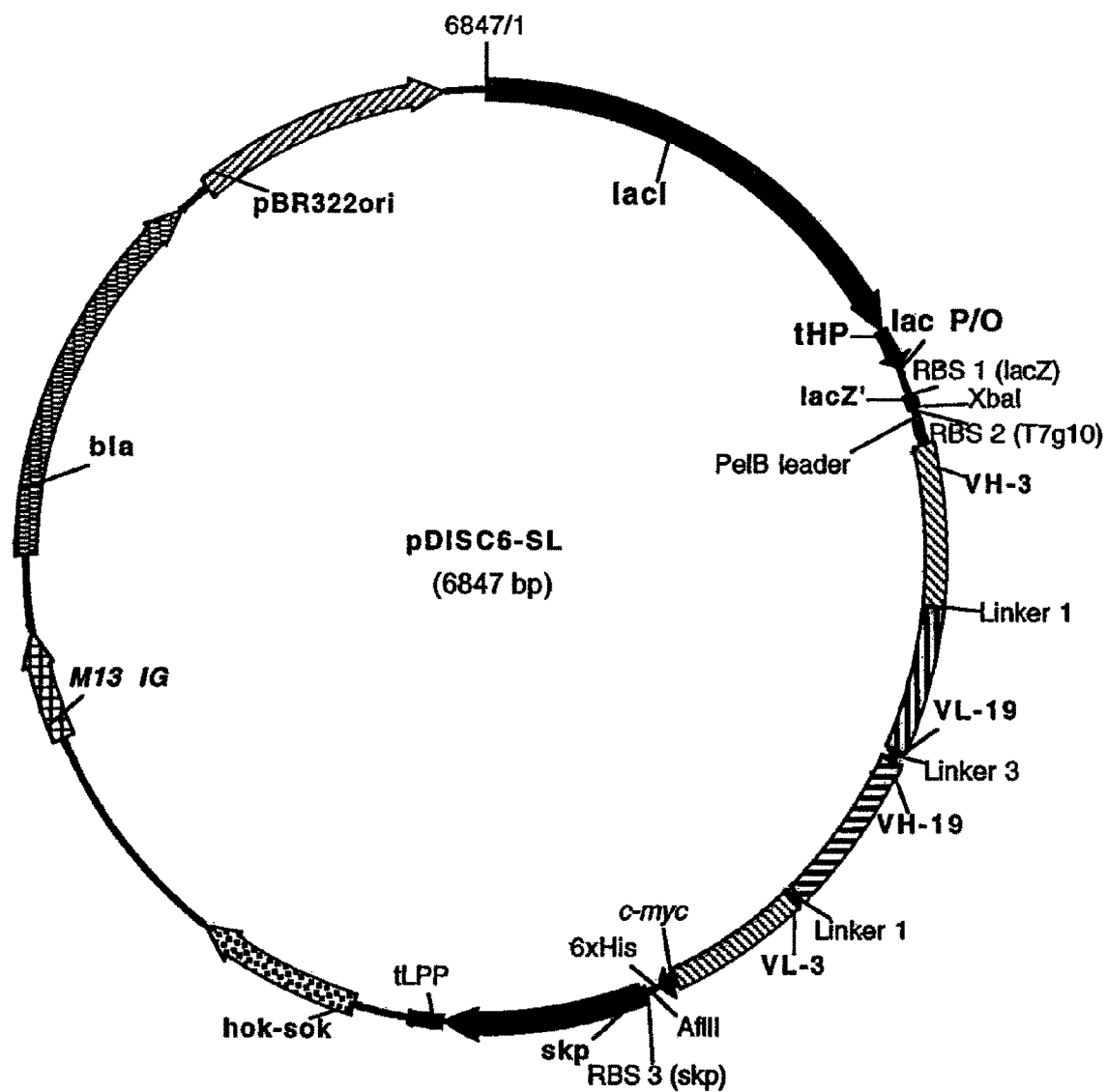

FIG. 10 shows a diagram of the expression plasmid pDISC6-SL. 6×His: sequence which codes for six C-terminal histidine residues; bla: gene which codes for β-lactamase responsible for ampicillin resistance; bp: base pairs: c-myc: sequence coding for an epitope which is recognized by the 9E10 antibody; hok-sok: plasmid-stabilized DNA locus; LacI: gene which codes for the Lac repressor; Lac P/O: wt lac-operon promoter/operator; LacZ': gene which codes for the α-peptide of β-galactosidase; linker 1: sequence which codes for a GlyGly dipeptide which links the $V_H$ and $V_L$ domains; linker 3: sequence which codes for a GlyGlyProGlySer SEQ ID NO: 18 oligopeptide linking the hybrid scFv fragments: M13 IG: intergenic region of the M13 bacteriophage; pBR322ori: origin of DNA replication; Pe1-B leader: signal peptide sequence of the bacterial pectate lyase; rbs: ribosome binding site originating from the *E. coli* lacZ gene (lacZ), from the bacteriophage TV gene 10 (T7g10) or from the *E. coli* skp gene (skp); skp: gene which codes for the bacterial periplasmic factor Skp/OmpH; tHP: strong transcription terminator; tIPP: transcription terminator; $V_H$ and $V_L$: variable region of the heavy and light chains.

DETAILED DESCRIPTION OF THE INVENTION

It is the object of the present invention to provide an antibody by means of which undesired immune responses can be avoided. Furthermore, it shall have a stability which makes it useable for therapeutic use.

Therefore, the subject matter of the present invention relates to a multi-valent $F_v$ antibody construct which has great stability. Such a construct is suitable for diagnostic and therapeutic purposes.

The present invention is based on the applicant's insights that the stability of an $F_v$ antibody construct can be increased if it is present in the form of a single-chain dimer where the four variable domains are linked with one another via three peptide linkers. The applicant also recognized that the $F_v$ antibody construct folds with itself when the middle peptide linker has a length of about 10 to 30 amino acids. The applicant also recognized that the $F_v$ antibody construct folds with other $F_v$ antibody constructs when the middle peptide linker has a length of about up to 10 amino acids so as to obtain a multimeric, i.e. multi-valent, $F_v$ antibody construct. The applicant also realized that the $F_v$ antibody construct can be multi-specific.

According to the invention the applicant's insights are utilized to provide a multi-valent $F_v$ antibody construct which comprises at least four variable domains which are linked with one another via peptide linkers 1, 2 and 3.

The expression "$F_v$ antibody construct" refers to an antibody which has variable domains but no constant domains.

The expression "multivalent $F_v$ antibody construct" refers to an $F_v$ antibody which has several, but at least four, variable domains. This is achieved when the single-chain $F_v$ antibody construct folds with itself so as to give four variable domains, or folds with other single-chain $F_v$ antibody constructs. In the latter case, an $F_v$ antibody construct is given which has 8, 12, 16, etc., variable domains. It is favorable for the $F_v$ antibody construct to have four or eight variable domains, i.e. it is bivalent or tetravalent (FIG. 1). Furthermore, the variable domains may be equal or differ from one another, so that the antibody construct recognizes one or several antigens. The antibody construct preferably recognizes one or two antigens, i.e. it is monospecific and bispecific, respectively. Examples of such antigens are proteins CD19 and CD3.

The expression "peptide linkers 1, 3" refers to a peptide linker adapted to link variable domains of an $F_v$ antibody construct with one another. The peptide linker may contain any amino acids, the amino acids glycine (G), serine (S) and proline (P) being preferred. The peptide linkers 1 and 3 may be equal or differ from each other. Furthermore, the peptide linker may have a length of about 0 to 10 amino acids. In the former case, the peptide linker is only a peptide bond from the COOH residue of one of the variable domains and the $NH_2$ residue of another of the variable domains. The peptide linker preferably comprises the amino acid sequence GG.

The expression "peptide linker 2" refers to a peptide linker adapted to link variable domains of an $F_v$ antibody construct with one another. The peptide linker may contain any amino acids, the amino acids glycine (G), serine (S) and proline (P) being preferred. The peptide linker may also have a length of about 3 to 10 amino acids, in particular 5 amino acids, and most particularly the amino acid sequence GGPGS (SEQ ID NO:18), which serves for achieving that the single-chain $F_v$ antibody construct folds with other single-chain $F_v$ antibody constructs. The peptide linker can also have a length of about 11 to 20 amino acids, in particular 15 to 20 amine acids, and most particularly the amino acid sequence $(G_4S)_4$, (SEQ ID NO:23) which serves for achieving that the single-chain $F_v$ antibody construct folds with itself.

An $F_v$ antibody construct according to the invention can be produced by common methods. A method is favorable in which DNAs coding for the peptide linkers 1, 2 and 3 are ligated with DNAs coding for the four variable domains of an $F_v$ antibody construct such that the peptide linkers link the variable domains with one another and the resulting DNA molecule is expressed in an expression plasmid. Reference is made to Examples 1 to 6. As to the expressions "$F_v$ antibody construct" and "peptide linker" reference is made to the above explanations and, by way of supplement, to Maniatis, T. et al., *Molecular Cloning, A Laboratory Manual*, Cold Spring Harbor Laboratory 1982.

DNAs which code for an $F_v$ antibody construct according to the invention also represent a subject matter of the present invention. Furthermore, expression plasmids which contain such DNAs also represent a subject matter of the present invention. Preferred expression plasmids are pDISC3×19-LL, pDISC3×19-SL, pPIC-DISC-LL, pPIC-DISC-SL, pDISC5-LL and pDISC6-SL. The first four were deposited with the DSMZ (Deutsche Sammlung fur Mikroorganismen and Zellen) [German-type collection for micro-organisms and cells] on Apr. 30, 1998 under DSM 12150, DSM 12149, DSM 12152 and DSM 12151, respectively.

Another subject matter of the present invention relates to a kit, comprising:
  (a) an $F_v$ antibody construct according to the invention, and/or
  (b) an expression plasmid according to the invention, and
  (c) conventional auxiliary agents, such as buffers, solvents and controls.

One or several representatives of the individual components may be present.

The present invention provides a multi-valent $F_v$ antibody construct where the variable domains are linked with one another via peptide linkers. Such an antibody construct distinguishes itself in that it contains no parts which can lead to undesired immune reactions. Furthermore, it has great stability. It also enables to bind several antigens simultaneously. Therefore, the $F_v$ antibody construct according to the invention is perfectly adapted to be used not only for diagnostic but also for therapeutic purposes. Such purposes can be seen as regards any disease, in particular a viral, bacterial or tumoral disease.

The invention is explained by the below examples. The following preparations and examples are given to enable those skilled in the art to more clearly understand and to practice the present invention. The present invention, however, is not limited in scope by the exemplified embodiments, which are intended as illustrations of single aspects of the invention only, and the methods which are functionally equivalent are within the scope of the invention. Indeed, various modifications of the invention in addition to those described herein will become apparent to those skilled in the art from the foregoing description and accompanying drawings. Such modification are intended to fall within the scope of the appended claims.

EXAMPLES

Example 1

Figure 2A:
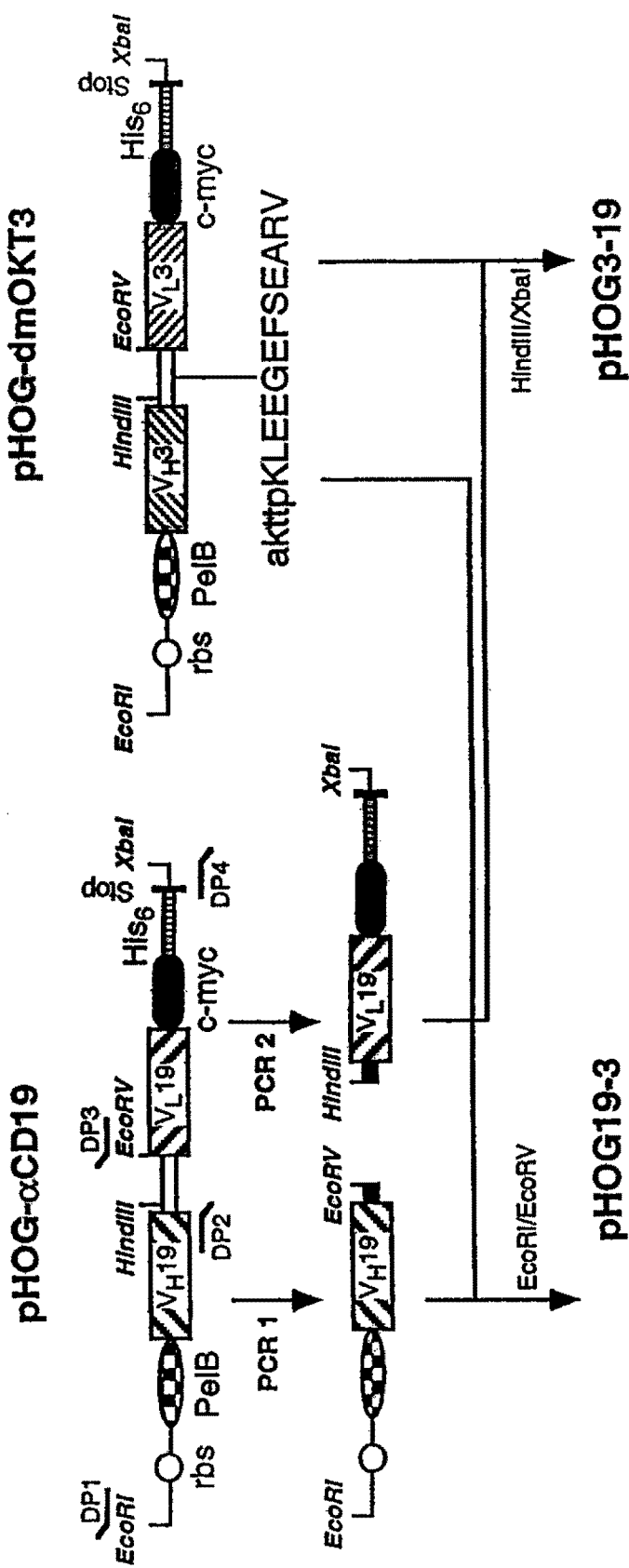
FIG. 2 shows the scheme for the construction of the plasmids pDISC3×19-LL and pDISC3×19-SL. c-myc: sequence coding for an epitope which is recognized by the antibody 9E1, His$_6$: sequence which codes for six C-terminal histidine residues; Pe1B: signal peptide sequence of the bacterial pectate lyase (Pe1B leader); rbs: ribosome binding site; Stop: stop codon (TAA); $V_H$ and $V_L$: variable region of the heavy and light chains; linker L3 (SEQ ID NO:18).
Figure 2B:
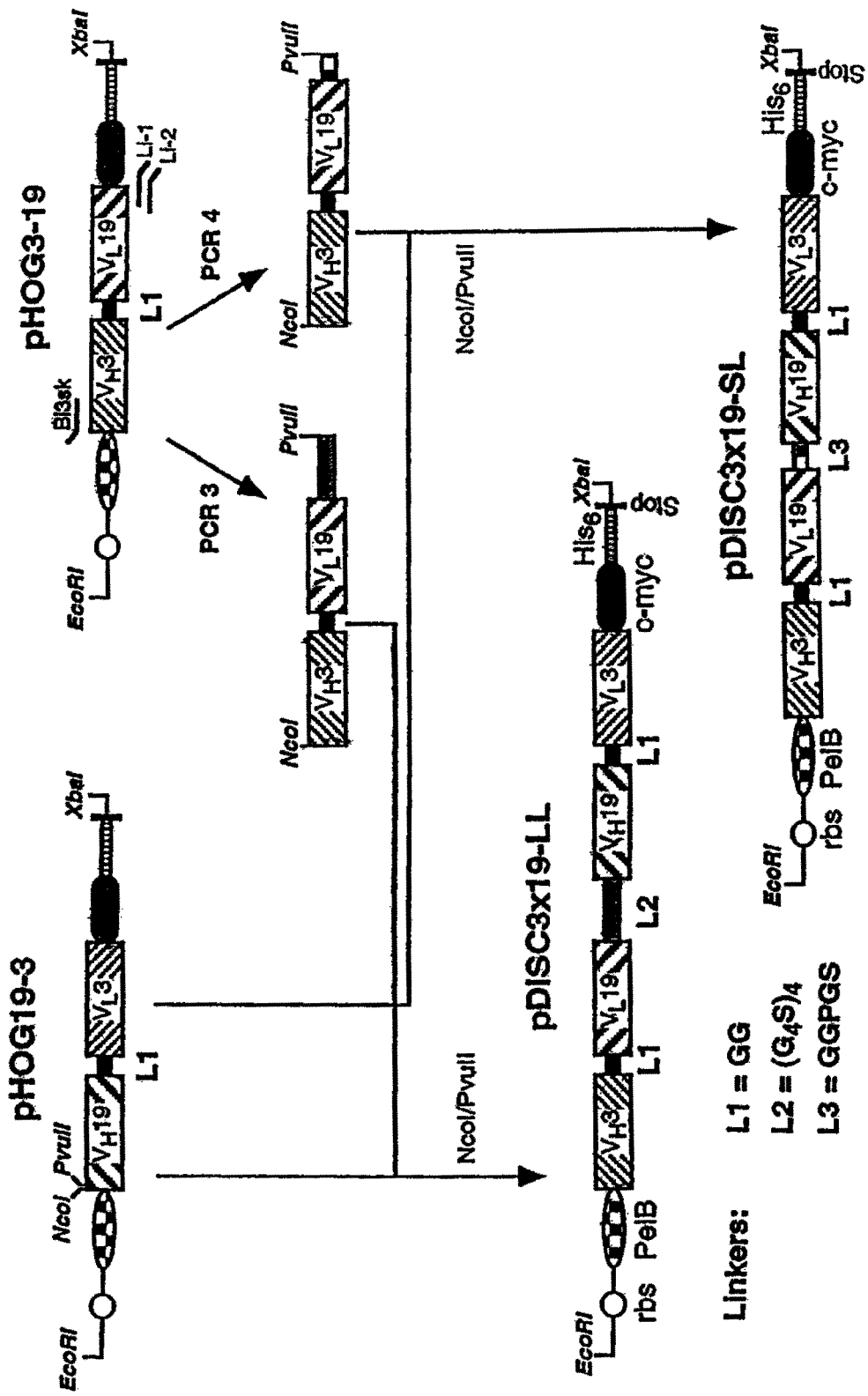
Figure 3:
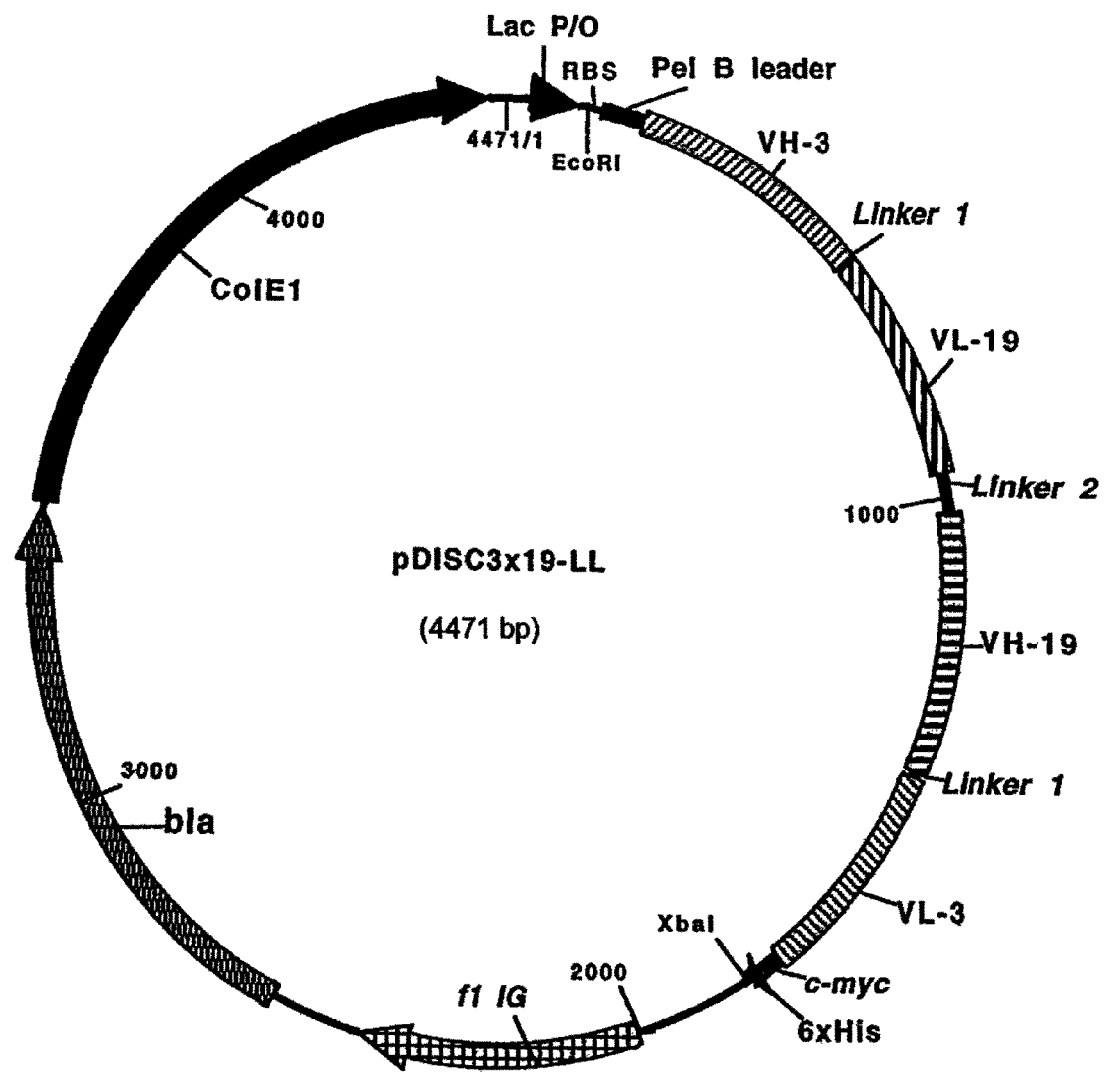
FIG. 3 shows a diagram of the expression plasmid pDISC3×19-LL. 6×His: sequence which codes for six C-terminal histidine residues; bla: gene which codes for β-lactamase responsible for ampicillin resistance; bp: base pairs; c-myc: sequence coding for an epitope which is recognized by the 9E10 antibody; ColE1: origin of the DNA replication; f1-IG: intergenic region of the bacteriophage f1; Lac P/O: wt lac-operon promoter/operator; linker 1: sequence which codes for a GlyGly dipeptide linking the $V_H$ and $V_L$ domains; linker 2: sequence coding for a (Gly$_4$Ser)$_4$ polypeptide which links the hybrid scFv fragments; Pe1-B leader: signal peptide sequence of the bacterial pectate lyase; rbs: ribosome binding site; $V_H$ and $V_L$: variable region of the heavy and light chains.
Figure 4:
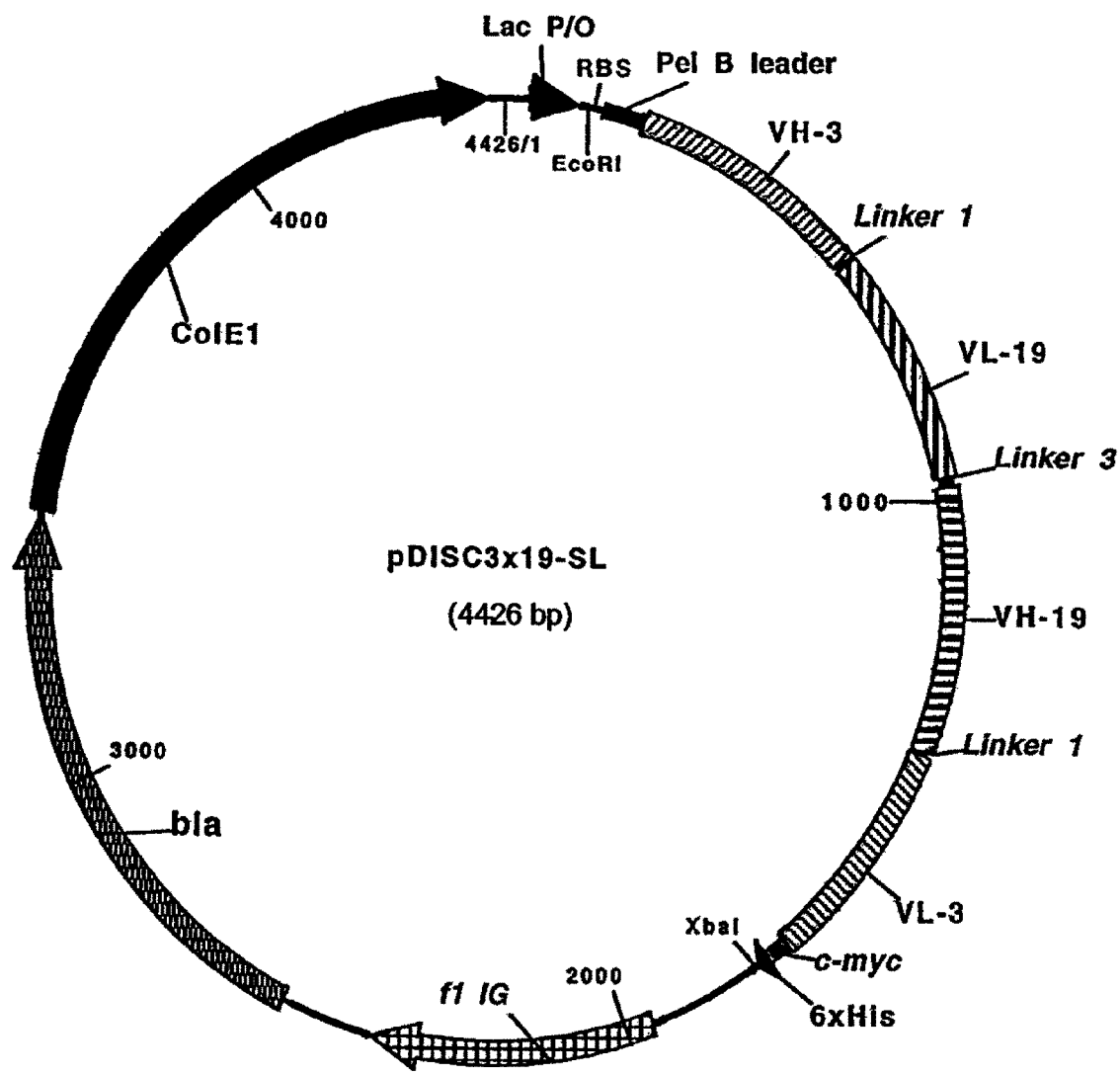
FIG. 4 shows a diagram of the expression plasmid pDISC3×19-SL. 6×His: sequence which codes for six C-terminal histidine residues; bla: gene which codes for β-lactamase which is responsible for the ampicillin resistance; bp: base pairs; c-myc: sequence coding for an epitope recognized by the 9E10 antibody; ColE1: origin of DNA replication; f1-IG: intergenic region of the bacteriophage f1; Lac P/O: wt lac-operon promoter/operator: linker 1: sequence which codes for a GlyGly dipeptide which links the $V_H$ and $V_L$ domains; linker 3: sequence which codes for a GlyGlyProGlySer SEQ ID NO: 18 oligopeptide which links the hybrid scFv fragments; Pe1-B leader: signal peptide sequence of the bacterial pectate lyase; rbs: ribosome binding site; $V_H$ and $V_L$: variable region of the heavy and light chains.

Construction of the Plasmids pDISC3×19-LL and pDISC3×19-SL for the Expression of Bivalent, Bispecific and/or Tetravalent, Bispecific $F_v$ Antibody Constructs in Bacteria The plasmids pHOG-αCD19 and pHOG-dmOKT3 which code for the scFv fragments derived from the hybridoma HD37 which is specific to human CD19 (Kipriyanov et al., 1996, J. Immunol. Meth. 196, 51-62) and from the hybridoma OKT3 which is specific to human CDS (Kipriyanov et al., 1997, Protein Eng. 10, 445-453), respectively, were used for the construction of expression plasmids for a single chain $F_v$ antibody construct. A PCR fragment 1 of the $V_H$ domain of anti-CD19, followed by a segment which codes for a GlyGly linker, was produced using the primers DP1,5'-TCACACA-GAATTCTTAGATCTATTAAAGAGGAGAAATTAACC (SEQ ID NO:12) and DP2, 5'-AGCACACGATATCACCGC-CAAGCTTGGGTGTTGTTTTGGC (SEQ ID NO:13) (FIG. 2). The PCR fragment 1 was cleaved by EcoRI and EcoRV and ligated with the EcoRI/EcoRV-linearized plasmid pHOG-dmOTK3 so as to produce the vector pHOG19-3. The PCR fragment 2 of the $V_L$ domain of anti-CD19, followed by a segment which codes for a c-myc epitope and a hexahistidinyl tail, was produced using the primers DPS, 5'-AGCACA-CAAGCTTGGCGGTGATATCTTGCTCACCCAAACTC CA (SEQ ID NO:14) and DP4,5'-AGCACACTCTAGAGA-CACACAGATCTTTAGTGATGGTGATGGT-GATGTGAGTTTA GG (SEQ ID NO:15). The PCR fragment 2 was cleaved by HindIII and XbaI and ligated with the HindIII/XbaI-linearized plasmid pHOG-dmOKT3 so as to obtain the vector pHOG3-19 (FIG. 2). The gene coding for the hybrid scFv-3-19 in the plasmid pHOG3-19 was amplified by means of PCR with the primers Bi3sk, 5'-CAGCCG-GCCATGGCGCAGGTGCAACTGCAGCAG (SEQ ID NO:16) and either Li-1,5'-TATATACTGCAGCTGCAC-CTGGCTACCACCACCACCGGAGC CGCCACCAC-CGCTACCACCGCCGCCAGAACCACCAC-CACCAGCGGCCGCAGCA TCAGCCCG (SEQ ID NO:17) for the production of a long flexible $(Gly_4Ser)_4$ (SEQ ID NO:23) inter-scFv linker (PCR fragment 3, FIG. 2) or Li-2,5'-TATATACT GCAGCTGCACCTGCGAC-CCTGGGCCACCAGCGGCCGCAGCATCAGCCCG (SEQ ID NO:5), for the production of a short rigid GGPGS linker (PCR fragment 4, FIG. 2). The expression plasmids pDISC3×19-LL and pDISC3×19-SL were constructed by ligating the NcoI/PvuII restriction fragment from pHOG19-3, comprising the vector framework and the NcoI/PvuII-cleaved PCR fragments 3 and 4, respectively (FIGS. 3, 4). The complete nucleotide and protein sequences of the bivalent and tetravalent $F_v$ antibody constructs are indicated in FIGS. 5 and 6, respectively.

Example 2

Construction of the Plasmids pPIC-DISC-LL and pPIC-DISC-SL for the Expression of Bivalent, Bispecific and/or Tetravalent, Bispecific $F_v$ Antibody Constructs in Yeast (A) Construction of pPIC-DISC-SL.

The vector pPICZαA (Invitrogen BV, Leek, Netherlands) for the expression and secretion of recombinant proteins in the yeast *Pichia pastoris* was used as a starting material. It contains a gene which codes for the *Saccharomyces cerevisiae* α-factor secretion signal, followed by a polylinker. The secretion of this vector is based on the dominant selectable marker, Zeocin™ which is bifunctional in both *Pichia* and *E. coli*. The gene which codes for the tetravalent $F_v$ antibody construct (scDia-SL) was amplified by means of PCR by the template pDISC3×19-SL using the primers 5-PIC, 5'-CCGT-GAATTCCAGGTGCAACTGCAG-CAGTCTGGGGCTGAACTGGC (SEQ ID NO:6) and pSEXBn, 5'-GGTCGACGTTAACCGACAAACAACA GATAAAACG (SEQ ID NO:7).

(B) Construction of pPIC-DISC-LL.

The construction of pPIC-DISC-LL was carried out on the basis of pPICZaA (Invitrogen BV, Leek, Netherlands) and pDISC3×19-LL (FIG. 3). The plasmid-DNA pPICZaA was cleaved by EcoRI. The overhanging 5'-ends were filled using a Klenow fragment of the *E. coli* DNA polymerase I. The resulting DNA was cleaved by Xba1, and the large fragment comprising the pPIC vector was isolated. Analogous thereto the DNA of pDISC3×19-LL was cleaved by NcoI and treated with a Klenow fragment. Following the cleavage using Xba1 a small fragment, comprising a gene coding for the bivalent $F_v$ antibody, was isolated. Its ligation with a pPIC-derived vector-DNA resulted in the plasmid pPIC-DISC-LL. The nucleotide and protein sequences of the bivalent $F_v$ antibody construct are shown in FIG. 8.

Example 3

Expression of the Tetravalent and/or Bivalent $F_v$ Antibody Construct in Bacteria E. coli XL1-blue cells (Strategene, La Jolla, Calif.) which had been transformed with the expression plasmids pDISC3× 19-LL and pDISC3×19-SL, respectively, were cultured overnight in 2×YT medium with 50/µg/ml ampicillin and 100 mM glucose (2×YT$_{Ga}$) at 37° C. 1:50 dilutions of the overnight cultures in 2×YT$_{GA}$ were cultured as flask cultures at 37° C. while shaking with 200 rpm. When the cultures had reached an OD$_{600}$ value of 0.8, the bacteria were pelleted by 10-minute centrifugation with 1500 g at 20° C. and resuspended in the same volume of a fresh 2×YT medium containing 50 pg/ml ampicillin and 0.4 M saccharose. IPTG was added up to a final concentration of 0.1 mM, and the growth was continued at room temperature (20-22° C.) for 18-20 h. The cells were harvested by 10-minute centrifugation with 5000 g at 4° C. The culture supernatant was held back and stored on ice. In order to isolate the soluble periplasmic proteins, the pelleted bacteria were resuspended in 5% of the initial volume of ice-cold 50 mM Tris-HCl, 20% saccharose, 1 mM EDTA, pH 8.0. Following 1 hour of incubation on ice with occasional stirring the spheroplasts were centrifuged with 30,000 g at 4° C. for 30 minutes, the soluble periplasmic extract being obtained as supernatant and the spheroplasts with the insoluble periplasmic material being obtained as pellet. The culture supernatant and the soluble periplasmic extract were combined and clarified by further centrifugation (30,000 g, 4° C., 40 min.). The recombinant product was concentrated by ammonium sulfate precipitation (final concentration 70% saturation). The protein precipitate was obtained by centrifugation (10,000 g, 4° C., 40 min.) and dissolved in 10% of the initial volume of 50 mM Tris-HCl, 1 M NaCl, pH 7.0. An immobilized metal affinity chromatography (IMAC) was carried out at 4° C. using a 5 ml column of chelating sepharose (Pharmacia) which was charged with $Cu^{2+}$ and had been equilibrated with 50 mM Tris-HCl, 1 M NaCl, pH 7.0 (starting buffer). The sample was loaded by passing it over the column. It was then washed with twenty column volumes of starting buffer, followed by starting buffer with 50 mM imidazole until the absorption at 280 nm of the effluent was at a minimum (about thirty column volumes). The absorbed material was eluted with 50 mM Tris-HCl, 1 M NaCl, 250 mM imidazole, pH 7.0.

The protein concentrations were determined with the Bradford dye binding test (1976, Anal. Biochem. 72, 248-254) using the Bio-Rad (Munich, Germany) protein assay kit. The concentrations of the purified tetravalent and bivalent $F_v$ antibody constructs were determined from the $A_{280}$ values using the extinction coefficients $\epsilon^{1\ mg/ml}=1.96$ and 1.93, respectively.

Example 4

Expression of the Tetravalent and/or Bivalent Antibody Construct in the Yeast Pichia pastoris Competent P. pastoris GS155 cells (Invitrogen) were electroporated in the presence of 10 µg plasmid-DNA of pPIC-DISC-LL and pPIC-DISC-SL, respectively, which had been linearized with SacI. The transformants were selected for 3 days at 30° C. on YPD plates containing 100 µg/ml Zeocin™. The clones which secreted the bivalent and/or tetravalent $F_v$ antibody constructs were selected by plate screening using an anti-c-myc-mAk 9E10 (1C Chemikalien, Ismaning, Germany).

For the expression of the bivalent $F_v$ antibody constructs and tetravalent $F_v$ antibody constructs, respectively, the clones were cultured in YPD medium in shaking flasks for 2 days at 30° C. with stirring. The cells were centrifuged resuspended in the same volume of the medium containing methanol and incubated for another 3 days at 30° C. with stirring. The supernatants were obtained after the centrifugation. The recombinant product was isolated by ammonium sulfate precipitation, followed by IMAC as described above.

Example 5

Characterization of the Tetravalent $F_v$ Antibody Construct and Bivalent $F_v$ Antibody Construct, Respectively (A) Size Exclusion Chromatography.

An analytical gel filtration of the $F_v$ antibody constructs was carried out in PBS using a superdex 200-HR10/30 column (Pharmacia). The sample volume and the flow rate were 200 µl/min and 0.5 ml/min, respectively. The column was calibrated with high-molecular and low-molecular gel filtration calibration kits (Pharmacia).

(B) Flow Cytometry.

The human $CD3^+/CD19^-$-acute T-cell leukemia line Jurkat and the $CD19^+/CD3^-$ B-cell line JOK-1 were used for flow cytometrie. $5 \times 10^5$ cells in 50 µl RPMI 1640 medium (GIBCO BRL, Eggestein, Germany) which was supplemented with 10% PCS and 0.1% sodium azide (referred to as complete medium) were incubated with 100 µl of the $F_v$ antibody preparations for 45 minutes on ice. After washing using the complete medium the cells were incubated with 100 µl 10 µg/ml anti-cmyc-Mak 9E10 (1C Chemikalien) in the same buffer for 45 minon ice. After a second wash cycle, the cells were incubated with 100 µl of the FITC-labeled goat-anti-mouse-IgG (GIBCO BRL) under the same conditions as before. The cells were then washed again and resuspended in 100 µl 1 µg/ml propidium iodide solution (Sigma, Deisenhofen, Germany) in complete medium with the exclusion of dead cells. The relative fluorescence of the stained cells was measured using a FACScan flow cytometer (Becton Dickinson, Mountain View, Calif.).

(C) Cytotoxicity Test.

The GD19-expressing Burkitt lymphoma cell line Raji and Namalwa were used as target cells. The cells were incubated in RPMI 1640 (GIBCO BRL) which was supplemented with 10% heat-inactivated PCS (GIBCO BRL), 2 mM glutamine and 1 mM pyruvate, at 37° C. in a dampened atmosphere with 7.5% $CO_2$. The cytotoxic T-cell tests were carried out in RPMI-1640 medium supplemented with 10% FCS, 10 mM HEPES, 2 mM glutamine, 1 mM pyruvate and 0.05 mM 2-ME. The cytotoxic activity was evaluated using a standard [$^{51}Cr$] release test; $2 \times 10^6$ target cells were labeled with 200 µCi Na [$^{51}Cr$] $O_4$ (Amersham-Buchler, Braunschweig, Germany) and washed 4 times and then resuspended in medium in a concentration of $2 \times 10^5$/ml. The effector cells were adjusted to a concentration of $5 \times 10^6$/ml. Increasing amounts of CTLs in 100 µl were titrated to $10^4$ target cells/well or cavity in 50 µl. 50 µl antibodies were added to each well. The entire test was prepared three times and incubated at 37° C. for 4 h. 100 µl of the supernatant were collected and tested for

[⁵¹Cr] release in a gamma counter (Cobra Auto Gamma; Canberra Packard, Dreieich, Germany). The maximum release was determined by incubation of the target cells in 10% SDS, and the spontaneous release was determined by incubation of the cells in medium alone. The specific lysis (%) was calculated as: (experimental release−spontaneous release)/(maximum release−spontaneous release)×100.

Example 6

Construction of the Plasmids pDISCS-LL and pDISC5-SL for the Expression of Bivalent, Bispecific and/or Tetravalent, Bispecific $F_v$ Antibody Constructs in Bacteria by High Cell Density Fermentation Expression vectors were prepared which contained the hok/sok plasmid-free cell suicide system and a gene which codes for the Skp/OmpH periplasmic factor for a greater production of recombinant antibodies. The skp gene was amplified by PCR using primers skp-1,5'-CGAATTCTTAAGATAAGAAGGAGTTTATTGT-GAAAAAGTGGTTATTAGCTGCAG G (SEQ ID NO:19) and skp-2,5'-CGAATTAAGCTTCATTATTTAACCT-GTTTCAGTACGTCGG (SEQ ID NO:20) using the plasmid pGAH317 (Hoick and Kleppe, 1988, Gene 67, 117-124). The resulting PCR fragment was cleaved by AflII and HindIII and inserted in the AflII/HindIII-linearized plasmid pHKK (Horn et al., 1996, Appl. Microbiol. Biotechnol. 46, 524-532) so as to obtain the vector pSKK. The genes obtained in the plasmids pDISC3×19-LL and pDISC3×19-SL and coding for the scFv antibody constructs were amplified by means of the primers fe-1,5'-CGAATTTCTAGATAAGAAGGAGAAAT-TAACCATGAAATACC (SEQ ID NO:21) and fe-2,5'-CGAATTCTTAAGCTATTAGTGATGGT-GATGGTGATGTGAG (SEQ ID NO:22). The XbaI/AflII-cleaved PCR fragments were inserted in pSKK before the skp insert so as to obtain the expression plasmids pDISC5-LL and pDISC6-SL, respectively, which contains tri-cistronic operons under the control of the lac promoter/operator system (FIGS. 9, 10).

```

What is claimed is:

1. A monospecific, homodimeric and tetravalent $F_v$ antibody formed by two single-chain $F_v$ monomers of the same kind, each of the single-chain $F_v$ monomer having the structure:

$V_H$-peptide linker 1-$V_L$-peptide linker 2-$V_H$-peptide linker 3-$V_L$, wherein with the proviso that each $F_v$ monomer does not have constant domains;

$V_H$ and $V_L$ are heavy chain and light chain variable domains of an antibody specific for an antigen, respectively;

peptide linker 1 is a peptide bond or has 1 to about 10 amino acids;

peptide linker 2 has about 3 to 10 amino acids;

peptide linker 3 is a peptide bond or has 1 to about 10 amino acids; and each $V_H$ of one of the single-chain $F_v$ monomers associates intermolecularly with each $V_L$ of the other single-chain $F_v$ monomer, thereby forming said homodimeric and tetravalent Fv antibody having four antigen binding sites for the same antigen.

2. The $F_v$ antibody of claim 1, wherein said peptide linker 1 and peptide linker 3 both have the amino acid sequence GG.

3. The $F_v$ antibody of claim 1, wherein said peptide linker 2 comprises the amino acid sequence GGPGS (SEQ ID NO: 18).

4. The $F_v$ antibody of claim 1, wherein the antigen for the $F_v$ antibody is CD3 or CD19.

5. A method for producing said Fv antibody of claim 1, comprising the steps of:

ligating DNAs encoding said four variable domains of said single chain Fv monomers with DNAs encoding peptide linker 1, peptide linker 2 and peptide linker 3 to produce a DNA encoding said single chain Fv monomer having the structure:

VH-peptide linker 1-VL-peptide linker 2-VH-peptide linker 3-VL with the proviso that each $F_v$ monomer does not have constant domains; and introducing the DNA encoding said single chain Fv monomer into an expression vector for said single-chain Fv monomer;

transforming a host cell with the expression vector for said monomer single-chain Fv monomer; and cultivating the host cell under conditions so that said single-chain Fv monomer is expressed.

6. A composition comprising said $F_v$ antibody of claim 1 for diagnosis and/or treatment of diseases.

* * * * *